US005908973A

United States Patent [19]

Abu-Bakar et al.

[11] Patent Number: 5,908,973

[45] Date of Patent: Jun. 1, 1999

[54] DNA ENCODING FRUIT-RIPENING-RELATED PROTEINS, DNA CONSTRUCTS, CELLS AND PLANTS DERIVED THEREFROM

[75] Inventors: Umi Kalsom Abu-Bakar; Sarah Louise Barton, both of Sutton Bonington, United Kingdom; Pedro Pablo Gallego-Veigas, Pontevedra, Spain; Julie Elizabeth Gray, Sheffield, United Kingdom; Donald Grierson, Shepshed, United Kingdom; Alexandra Louise Lowe, Sutton Bonington, United Kingdom; Steve Picton, Warrington, United Kingdom; Lee Colin Whotton, Sutton Bonington, United Kingdom

[73] Assignee: Zeneca Limited, London, United Kingdom

[21] Appl. No.: 08/522,421

[22] PCT Filed: Mar. 22, 1994

[86] PCT No.: PCT/GB94/00581

§ 371 Date: Jan. 11, 1996

§ 102(e) Date: Jan. 11, 1996

[87] PCT Pub. No.: WO94/21794

PCT Pub. Date: Sep. 29, 1994

[30] Foreign Application Priority Data

| | | | |
|---|---|---|---|
| Mar. 22, 1993 | [GB] | United Kingdom | 9305859 |
| Mar. 22, 1993 | [GB] | United Kingdom | 9305860 |
| Mar. 22, 1993 | [GB] | United Kingdom | 9305862 |
| Mar. 22, 1993 | [GB] | United Kingdom | 9305865 |
| Mar. 22, 1993 | [GB] | United Kingdom | 9305866 |
| Mar. 22, 1993 | [GB] | United Kingdom | 9305867 |
| Mar. 22, 1993 | [GB] | United Kingdom | 9305868 |
| Mar. 22, 1993 | [GB] | United Kingdom | 9305869 |
| Jul. 12, 1993 | [GB] | United Kingdom | 9314351 |
| Oct. 12, 1993 | [GB] | United Kingdom | 9320988 |

[51] Int. Cl.[6] .............................. A01H 1/02; A01H 5/00; A01H 5/10; C12N 5/14

[52] U.S. Cl. ...................... 800/295; 435/320.1; 435/419; 435/468; 536/23.2; 536/23.6; 800/260; 800/278

[58] Field of Search ............................ 435/320.1, 172.3, 435/410, 411, 419; 536/24.1, 23.2, 23.6; 800/205, DIG. 9, DIG. 52, DIG. 44, 250; 47/58, DIG. 1

[56] References Cited

U.S. PATENT DOCUMENTS 5,328,999 7/1994 Bennett et al. ........................ 536/24.5

OTHER PUBLICATIONS

Gray J, et al. "Molecular biology of fruit ripening and its manipulation with antisense genes." Plant Mol. Biol. 19: 69–87, 1992.

Iusem ND, et al. Tomato (*Lycopersicon esculentum*) transcript induced by water deficit and ripening. Plant Physiol. 102: 1353–1354, Aug. 1993.

Iusem ND, et al. GenBank accession No.L08255, 1993.

*Primary Examiner*—Douglas W. Robinson
*Assistant Examiner*—Amy J. Nelson
*Attorney, Agent, or Firm*—Pillsbury Madison & Sutro, LLP

[57] ABSTRACT

DNA constructs comprising DNA sequences encoding fruit-ripening-related proteins may be transformed into plants to modify plant characteristics (particularly fruit quality). New DNA sequences are disclosed; cDNA and genomic clones have been deposited; new fruit-ripening-related promoter sequences may also be obtained. Sense and antisense constructs for plant transformation are described. Genetically modified plants may be used to produce improved fruit and may also be used in breeding programs to produce hybrid seed.

12 Claims, 11 Drawing Sheets

EcoRI
EcoRI
NPTII
LB
RB
pSLJ44024A
ERT 1 Antisense Construct
280 bp EcoRI/BamHI
fragment
STEP 2
EcoRI fragment, no
CaMv 35S terminator
EcoRI
BamHI
BamHI
EcoRI
CaMv
35S prom
CaMv
35S term
pDH51
340 bp BamHI fragment
STEP 1
BamHI
BamHI
5'
3'
EcoRI
XhoI
pBluescript
pERT 1

EcoRI
NPTII
LB
SacI
RB
ERT 1 Antisense Construct
pSLJ44026B
EcoRI/SacI fragment
STEP 2
BamHI
BamHI
EcoRI
SacI
CaMv
35S prom
CaMv
35S term
pDH51
340 bp BamHI fragment
BamHI
STEP 1
5'
3'
EcoRI
XhoI
pERT 1
pBluescript ERT 1b Antisense Construct 490 bp BamHI fragment ligated to BglII cut vector pERT 1b EcoRI
EcoRI
NPTII
LB
RB
pSLJ44024A
ERT 10 Antisense Construct
290 bp EcoRI/BamHI
fragment
STEP 2
EcoRI fragment, no
CaMv 35S terminator
BamHI
EcoRI
BamHI
EcoRI
CaMv
35S prom
CaMv
35S term
pDH51
350 bp BamHI fragment
STEP 1
BamHI
BamHI
5'
3'
EcoRI
XhoI
pBluescript
pERT 10

PvuII/EcoRI
ERT 10 Antisense Construct
NPTII
SacI
LB
RB
pSLJ44026B
STEP 2
PvuII/SacI fragment ligated to EcoRI/SacI cut vector (EcoRI site blunted using Klenow)
BamHI
PvuII
CaMv 35S prom
CaMv 35S term
SacI
pDH51
350 bp BamHI fragment
BamHI
STEP 1
5'
3'
EcoRI
XhoI
pBluescript
pERT 10

EcorI
NPTII
LB
SacI
RB
ERT 13 Sense Construct
pSLJ44026B
STEP 2
SspI
XhoI
EcoRI/SacI fragment
EcoRI
SacI
CaMv 35S prom
CaMv 35S term
pDH51
180 bp SspI/XhoI sense fragment ligated to SmaI/SalI cut vector (fragment includes poly A+)
SspI
XhoI
STEP 1
5'
3'
EcoRI
XhoI
pBluescript
pERT 13

EcoRI
NPTII
LB
SacI
RB
ERT 14 Antisense Construct
pSLJ44026B
EcoRI/SacI fragment
STEP 2
DraI
BamHI
EcoRI
CaMv
35S prom
CaMv
35S term
SacI
pDH51
300 bp BamHI/DraI fragment
ligated to BamHI/SmaI
cut vector
BamHI
DraI
STEP 1
5'
3'
EcoRI
XhoI
pERT 14
pBluescript EcoRI
SacI
NPTII
LB
RB
pSLJ44026B
ERT 15 Antisense Construct
STEP 2
EcoRI/SacI fragment
PstI
PstI
EcoRI
SacI
CaMv
35S prom
CaMv
35S term
pDH51
730bp PstI fragment
PstI
STEP 1
5'
3'
EcoRI
XhoI
pBluescript
pERT 15

PvuII/EcoRI
SacI
ERT 16 Antisense Construct
NPTII
LB
RB
pSLJ44026B
STEP 2
PvuII/SacI fragment ligated to EcoRI/SacI cut vector (EcoRI site was blunted using Klenow)
PvuII
XbaI
PvuII
SacI
CaMv 35S prom
CaMv 35S term
pDH51
PvuII
STEP 1
XbaI
5'
3'
EcoRI
XhoI
250bp XbaI/PvuII fragment ligated to XbaI/SmaI cut vector
pBluescript
pERT 16

EcoRI
SacI
NPTII
LB
RB
ERT 17 Antisense Construct
pSLJ44026B
STEP 2
EcoRI/SacI fragment
NstI
PstI
EcoRI
SacI
CaMv
35S prom
CaMv
35S term
pDH51
600 bp PstI/NsiI fragment
ligated to PstI cut vector
NstI
STEP 1
PstI
5'
3'
EcoRI
XhoI
pBluescript
pERT 17

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
(A) LENGTH: 1669 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: ERT1B (xi) SEQUENCE DESCRIPTION: SEQ ID NO:1:

```
TAGAAAGAAA ACAGAGTGTA GTACTGGTAC CACACCCATA CCAGGGGCAT TTAACACCAA    60

TGCTACAGCT TGGTAGTATC CTTCATTCAC AAGGCTTTTC TGTTATAGTT GCACATACTC   120

AATACAATAC TCCTAATTAT TCCAATCATC CACAATTCGT CTTCCATTCT ATGGATGACG   180

GATTACAGGG AATCGACATG TCATTCCCGA GTTTAGAAAA CATATATGAT ATGAACGAAA   240

ACTGCAAGGC GCCTCTCAGA AACTACCTTG TTAGTATGAT GGAAGAGGAA GGTGATCAGC   300

TTGCTTGTAT CGTTTATGAC AACGTCATGT TCTTTGTCGA TGATGTAGCG ACTCAGTTGA   360

AGCTTCCCAG CATTGTCCTG CGCACTTTCA GCGCTGCGTA TTTGCACTCT ATGATCACCA   420

TTTTACAGCA ACCTGAAATA TATTTACCTT TTGAAGATTC TCAGCTGCTG GATCCGTTAC   480

CGGAGCTTCA TCCCTTGAGA TTTAAGGATG TACCGTTTCC TATCATCAAT AATACAGTTC   540
```

```
CAGAACCGAT ACTAGACTTC TGTAGAGCAA TGAGTGATAT AGGATCATCT GTCGCGACTA    600

TATGGAACAC GATGCAAGAC TTGGAGAGTT CAATGTTGTT ACGCCTTCAA GAACATTACA    660

AGGTGCCCTT TTTTCCAATA GGCCCGGTAC ACAAAATGGC ATCTTTGGTC TCATCGACTA    720

GCATACTAGA AGAAGACAAT AGCTGCATCG AGTGGCTCGA TAGACAAGCC CCTAACTCTG    780

TTCTCTATGT CAGCTTGGGT AGCCTAGTGA GGATTGATCA CAAAGAGTTG ATTGAGACTG    840

CTTGGGGATT AGCTAATAGC GATCAACCGT TCTTGTGGGT TATTCGACCT GGCTCTGTCT    900

CTGGCTTTCA ATGTGCTGAG GCACTGCCTG ATGGTTTTGA GAAAATGGTA GGAGAAAGAG    960

GACGAATAGT GAAATGGGCA CCACAAAAAC AGGTGCTTGC ACATCCCGCG GTAGCAGGGT   1020

TTTTCACTCA TTGTGGTTGG AATTCTACGC TTGAAAGTAT ATGTGAAGAA GTCCCTATGG   1080

TGTGCAGGCC ATTTCTAGCA GACCAACTGG TGAACGCAAG GTATCTGAGC CAAATATACA   1140

AGGTTGGGTT CGAATTGGAG GTTATCGAGA GAACGGTCAT AGAGAAAACA ATAAGAAAAC   1200

TCATGTTAAG TGAAGAAGGC AAAGATGTGA AGAAAAGAGT AGCAGACATG AAACAAAAGA   1260

TAGTTGCTGG AATGCAGATT GATTGCACTT CACATAAGAA TCTGAATGAT TTGGTAGACT   1320

TCATTTCTGC CTTGCCATCA CGACTCGCTC CGCCAACGCC TGTCTTTGGG GCAATCATGA   1380

GCTCAAACCA CATAGCAAGC AAGTGTATCA TAGAGTCTTG AAGTTATTTT TGAGCTCAAA   1440

CCATATTTCT GTGGCCCCTT AGCTTGGCAA GACAATAAGT CCTTAATCAC AAAAGGAAGA   1500

ATAAGATAAG AAGTGAACTT TTCATAAATC CATGGTGCAA ATGCTGAAGC AATTTACTTT   1560

AGTTTGTTGA TTGGTTTATA AGTTGGGAAC CTTGACATAT TGTTTTCTAG TTGGTAGGAA   1620

AATATTTTCG TGGAAAATAA ATGATTTTCA AAAAAAAAAA AAAAAAAAA              1669
```

(2) INFORMATION FOR SEQ ID NO:2:

(i) SEQUENCE CHARACTERISTICS:
(A) LENGTH: 944 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: ERT10

(xi) SEQUENCE DESCRIPTION: SEQ ID NO:2:

```
GAATCATCGC TGCCGCTCGT CGAATCGATC GATTGCAATC TCTATGTGAT GAAATCAACT     60

CGAATTCATC GAACGGATCG ACGAAGTCGA GTCAGGATTT ACGTGCCGTA GCGATTGAGC    120

TTGACGTTAG CGCTAATGGT TCTGCCATTG AAGCCGCCGT ACAGAAAGCT TGGGATGCAT    180

TTGGACGTAT CGACGGTTTG GTTAATAACG CCGGCTTTCG AGGCAGTGTG CTTTCTCCAC    240

TGGAGTTGTC GGAGGAGGAA TGGGAGAAGA TCCACAAAAC GAACTTAAGA GGGGCATGGT    300

TGGTGACCAA ATATGTTTGT ATGCATATGC GCGCTGCTAA TCAAGGAGGA TCCATAATCA    360

ATATCTCTTC TATCGCTGGT ATTAATCGTG GACAACTACC AGGTAGTCTT GCTTATACGT    420

CTTCAAAGGA AGCTCTCAAC AGCATTACAA AGGTGTTGGC CCTCGAATTG GGACCATACA    480

AGATCAGAGT GAACTCAATA TCACCTGGAC TTTTCAAATC TGAGATAACA GAGGGTCTCA    540

TACAAAAAGA CTGGATTAAA AACATTGAAC TGAGAACTAT TCCGTTGAGA ACACATGGAA    600

CATCACATCC CGCTTTAACT TCAGTTGTAC GTTACCTGAT CCACGATTCC TCGGAATATG    660

TTTCAGGTAA CATGTTCATA GTAGATGCAG GAGCTACTTT ACCCGGTGTC CCGATTTTCT    720

CATCCCTCTA GTATAGAGAA AACAAATTAG AAAAATAAGG ATGGAAAATG GAAATGTTTG    780
```

```
GGAAAGAACA GAGGCTTTAC TTTGGTTGCC TAAAAGAAAA TTTTATGTTT TTGTTTTGCT    840

CATGGAATTG TTTTTATATT TGTATCTGTT ATACCATTAA TTGAAATTAA TTAAACTCCT    900

ATGAAGTAAA GTTTGTTGCT TTTAAAAAAA AAAAAAAAAA AAAA                     944
```

(2) INFORMATION FOR SEQ ID NO:3:

(i) SEQUENCE CHARACTERISTICS:
(A) LENGTH: 334 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: ERT13

(xi) SEQUENCE DESCRIPTION: SEQ ID NO:3:

```
TTTTTTTTTT TTTTTTATAT TGAAATTTGG TTGAGTTTAT TGAGTTTTTT AGTTGAGTAT     60

TTTATTTACT GCTACTATTA TTATTACTAA AACTATATTT TAATATAATA TGGTTACAAT    120

GAGGGCATAT GTTAATATTT ATATATGCCT AGGTCTAGGT GGTCGGGTGG GATATTTTAC    180

ATAGTTTTTT TTTAAAGCTA TGTGTGTGTA ATCTTGTCCA GGGTTCTGTT TGTCATGGTT    240

TGATTAAAGA TGATATGAGA TTTGATCTCT AGTTTATTAT AATAATAAAG GGGTAATAAC    300

TTTTTTTTGT TGTTAAAAAA AAAAAAAAAA AAAA                                334
```

(2) INFORMATION FOR SEQ ID NO:4:

(i) SEQUENCE CHARACTERISTICS:
(A) LENGTH: 617 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: ERT14

(xi) SEQUENCE DESCRIPTION: SEQ ID NO:4:

```
CAACTAATAC TTAGACGACC GAGCCCCTTG CACAAAAAGG AATTGGCAGA ACGGTGAGCA     60

CCAAATCGTT GCCCCAAAAT TCCATTGCTG ACGAGTGACG AGGGAAGCGA GAAGCTAACA    120

AGATGCTGCC ACAGCGGATG AAAAAGGTTA TGACAGACAA CCCAAAGAAG TTAGCCAATT    180

TGATTGACCT AGTAAATCTC CCTTCAACAC TTAGAGAGTT CATGGGTCAG TCACAGACCT    240

CCCGCTTGGG TTGTTTTAAA CGTGTCTGGT CTTACATCAA AGAAAACAAT CTCCAGGATC    300

CGAACAACAA GAACTTGGTT AATTGCGATG AAAAGTTGAA GACTGTGTTG TTGGGTAAGC    360

CCCAGGTTGA GCTTACTGAA CTGCCAACGC TGATCAAGTT GCACTTCCCC AAGCAACCAA    420

GATGATTGAG TTTATTGTAA TGTTTAATCT TAGTGCTTAA TCTTCGAACA CTATATAGAC    480

TCCACAGATT TTACGAAGAG TTAGTCTGAT TAAGTATCCT GGTAAAATGA CTTGTCTTAT    540

GAGTTACTAG TCAAAGCTCT ACAAGCAGAA GCAGCTCTAT AGTTTTGCGT TTTGCCATAA    600

AAAAAAAAAA AAAAAAA                                                   617
```

(2) INFORMATION FOR SEQ ID NO:5:

(i) SEQUENCE CHARACTERISTICS:
(A) LENGTH: 1747 base pairs
(B) TYPE: nucleic acid
(C) STRANDEDNESS: single (D) TOPOLOGY: linear (ii) MOLECULE TYPE: cDNA (vi) ORIGINAL SOURCE:
(A) ORGANISM: ERT15

(xi) SEQUENCE DESCRIPTION: SEQ ID NO:5:

```
GATAACTTTT GATAGTACAA AGGGCCGTTT AATAGTACTT TGCGTCGAGC AAATGCAAAA     60
CTCAGATAGT GGATCAATTG CATTTTCTTC GAGGGCTGGA TCATCTTCTC AACGGACTTC    120
ACCTTTCCGT GAGGTTGGTG GATATGCTGC CGAACAGCTG TCTAGCAGTA GTATCTGTAG    180
CAGTCCTGAT GATAACAGTT GTGACGGGAT TAAGCTTGAG GAGAGTGAAG CATGGCACTT    240
AAGATTAGGT TATTCAACCA CTTGGCCTGG AATGGTGCTT GCAGTCTGCC CTTATCTTGA    300
TCGTTTTTTC TTGGCCTCTG CGGCTAATTG TTTCTATGTT TGTGGTTTTC CAAATGACAA    360
TGCCCAAAGA GTCAGACGCT TAGCAGTAGG AAGAACACGG TTCATGATCA TGACTCTTAC    420
GGCACACTTC ACTAGAATTG CTGTTGGTGA TTGTCGTGAT GGCATCCTTT TCTACTCGTA    480
TCAAGAGGAT TCAAGAAAAC TAGATCAAAT TTACTGTGAC CCTGTCCAGA GGTTAGTTTC    540
TGATTGCACT CTTATGGATG GAGACACAGC TGCCGTTTCA GATCGAAAGG GGAGTTTTGC    600
AATTTTATCA TGTCTGAATT ACATGGAAGA TAATTTCAAC AGTCCAGAAC GCAATCTAGC    660
TCAAACTTGT TCATTCTACA TGGGCGAGAT AGCTATAAGA ATTCGAAAGG GGTCATTCTC    720
CTATAAACTT CCTGCAGATG ATGCACTTAG GGGCTGTCAA GCTACCAGCA TTGTCGGTGA    780
CATATCACAA AATAGTATCA TGGCTAGTAC GCTTTTAGGG AGCATAATTA TTTTTATTCC    840
TCTTACTAGG GAGGAATATG ATCTCTTAGA AGCAGTACAG GCCAGGCTTG TCATCCATCC    900
GCTGACTGCT CCTATTTTGG GAAATGACCA TACTGAATAT CGTTGTCGTG GAAGTATGGC    960
TAGGGTACCT AAAGCTCTGG ATGGTGATAT GCTTGCTCAG TTCTTGGAGC TTACTAGTAT   1020
GCAACAAGAA GCTGTATTAG CATTGCCTCT TGGCGCACAA AACACAATTA TGTTCAATTC   1080
GAAGCAATCT CCTGATCCAA TTACTGTTAA TCAGGTTGTG CGACTGCTAG AACGAATTCA   1140
TTATGCCCTG AACTGAATAT CAGGTTTATC TTTGTCCTGA TGCTTTGAGA GCTGTTTACT   1200
TGGTCTTTGA TTGACCGCGA AATCAAGTGG CCTTTGCTAG TGCCAATTGC CTATCTGTTC   1260
ATATTTTTGG AAGCAAGCAA GGTGATTATC TGTGATTGCC AGATGATGAT TGGAGCTGGG   1320
TTTAACATTG TCTACATGCA GGCTATTCTG GTTTGTTTCG CTGTTGTTGG GTTGGGAGTT   1380
GGGAGCTAGG TTGTGTGGAT TCTTCACTCT CGATGTTGCA CCCATGTCGG ATTCTCCAAC   1440
AATACACTAC TTTTGAAGAA GTATTCGGCA TGCATGAGTT GACAATTTTT TAAAGAGTTC   1500
AAGCAATGTG GATTGGGGTA ATGCAGAAAT AATTTTGCAG GGCGCTTCCT TCATGGTAAT   1560
AGTCTGTACC CAGTTTTGTA GCTTTTCACT TAATTGTTGT AAATATATGT TTAGCGGCCT   1620
CGATAGACAC AGTTATTCAA TATTTATTTG ATAAAATAAT CGAGGTGCTT CAAAGAAAAA   1680
AAAAAGGCAA AAATTAAAAC ATGAACCTCG ATTTAATTGG TCAGAGTAAA AAAAAAAAAA   1740
AAAAAAA                                                             1747
```

(2) INFORMATION FOR SEQ ID NO:6:

(i) SEQUENCE CHARACTERISTICS:
(A) LENGTH: 641 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: ERT16B (xi) SEQUENCE DESCRIPTION: SEQ ID NO:6:

```
GAGAAACACC ACCACCACCA CCTGTTCCAC CACAAGGACA AGGCGGAGGA GGGCCCCCGT     60
CGACTACGAA AAAGAAATCA AACACCATAA ACATCTCGAG CAAATCGGTA AACTTGGCAC    120
TGTTGCTGCC GGTGCCTACG CCTTGCATGA GAAACATGAG GCAAAGAAAG ATCCAGAACA    180
TGCACACAAA CACAAGATAG AGGAAGAGAT AGCAGCAGCT GCTGGTTGGG GCAGGTGGAT    240
TTGCATTCCA TGAGCATCAT GAGAAAAAAG ATGCCAAGAA AGAAGAAAAA AAAGCTGAGG    300
GGGGACACCA CCATCTCTTC TAAATTGTTA TTTTAGTTAC ATTTTTAATA TTCGTGGAAT    360
TTCCATATTT GGTATAAGTG TTGTGTCATC TTATCATATA TCGTGCATAA TAACAATAAA    420
TTTAGTGTGA TATTATAAAT GGATCGAGTT AAAAAAAAAG AGCAAAGTCA AAATATATTT    480
TACCAATCTC GTTGATGTAA AGAAGGATGT ATTGTGATTT CCAAAATGAT CATGTGTGTT    540
TTGGACTTTC CTCGCAATCT TCTGTTGAAT TACCTTGTAA AATGTTGCTT TTTTAAGTGG    600
TGTAATAAAT AATGAGTTTT CTAGTGAAAA AAAAAAAAAA A                       641
```

(2) INFORMATION FOR SEQ ID NO:7:

(i) SEQUENCE CHARACTERISTICS:
(A) LENGTH: 686 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: ERT17

(xi) SEQUENCE DESCRIPTION: SEQ ID NO:7:

```
ATTTGGTCTG CTATGGCATC CAAGCGGATT CTCAAGGAGC TTAAGGATCT CCAGAAAGAT     60
CCTCCTACCT CTTGCAGTGC TGGCCCAGTA GCTGAAGATA TGTTCCATTG GCAAGCAACA    120
ATCATGGGTC CAGCTGACAG TCCCTATTCT GGTGGAGTGT TTCTTGTTAC TATTCATTTT    180
CCACCTGACT ATCCATTCAA GCCACCAAAG GTAGCTTTCA GGACAAAGGT TTTCCACCCG    240
AACATCAATA GCAATGGCAG CATTTGCCTT GACATTTTGA AGGAACAGTG GAGCCCTGCA    300
CTTACCATCT CCAAGGTACT GCTCTCTATC TGTTCTCTGC TGACAGACCC TAATCCCGAT    360
GACCCTTTGG TGCCGGAGAT TGCTCATATG TACAAAACTG ATAGGAGCAA GTATGAGACA    420
ACTGCCCGGA GCTGGACTCA AAAATTTGCC ATGGGATAGT TGCTGTGACC ATCTCTGTCC    480
CTGCTGTGGT ATTTTGTATT ATCTATCGAA TAGTTGCTGT GACCATCGGG GTCTGATTCC    540
CTGCTGTGGT ATTTAGTAGT TTATATATTA TGTATTATGA AATTGTGTTC TTATGCATAA    600
TCAAAACTTA AAAGGCGGGA AAGTCGAACA GGTTCGTCGT GAAACAATTT GATTTTCTCT    660
TTGCTTGCAA AAAAAAAAAA AAAAAA                                        686
```

(2) INFORMATION FOR SEQ ID NO:8:

(i) SEQUENCE CHARACTERISTICS:
(A) LENGTH: 1783 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: ERTD1

(xi) SEQUENCE DESCRIPTION: SEQ ID NO:8:

```
AAAAAATGGT GTTAACAACG ACGTCGATAA GAGATTCAGA AGAGAGCTTG CACTGTACAT     60
TTGCATCAAG ATATGTACAG GAACCTTTAC CTAAGTTCAA AATGCCTAAA AAATCCATGC    120
CGAAAGAAGC AGCTTATCAG ATTGTAAACG ACGAGCTTAT GTTGGATGGT AACCCCAGGT    180
TGAATTTAGC TTCCTTTGTT AGCACATGGA TGGAGCCCGA GTGCGATAAG CTCATCATGT    240
CATCCATTAA TAAAAACTAT GTCGACATGG ATGAGTATCC TGTCACCACT GAACTTCAAA    300
ATAGATGTGT TAACATGTTA GCACATCTTT TCCATGCCCC GGTTGGTGAT GATGAGACTG    360
CAGTTGGAGT TGGTACAGTG GGTTCATCAG AGGCAATAAT GCTTGCTGGC CTTGCTTTCA    420
AACGCAAATG GCAATCGAAA AGAAAAGCAG AAGGCAAACC TTTCGATAAG CCTAATATAG    480
TCACTGGAGC TAATGTGCAG GTCTGCTGGG AAAAATTTGC AAGGTATTTT GAGGTTGAGT    540
TGAAGGAGGT GAAACTAAAA GAAGGATACT ATGTAATGGA CCCTGCCAAA GCAGTAGAGA    600
TAGTGGATGA GAATACAATA TGTGTTGCTG CAATCCTTGG TTCTACTCTG ACTGGGGAGT    660
TTGAGGATGT GAAGCTCCTA AACGAGCTCC TTACAAAAAA GAACAAGGAA ACCGGATGGG    720
AGACACCGAT TCATGTCGAT GCTGCGAGTG GAGGATTTAT TGCTCCTTTC CTCTGGCCAG    780
ATCTTGAATG GGATTTCCGT TTGCCTCTTG TGAAAAGTAT AAATGTCAGC GGTCACAAGT    840
ATGGCCTTGT ATATGCTGGT GTCGGTTGGG TGATATGGCG GAGCAAGGAA GACTTGCCCG    900
ATGAACTCGT CTTTCATATA AACTACCTTG GGTCTGATCA GCCTACTTTT ACTCTCAACT    960
TCTCTAAAGG TTCCTATCAA ATAATTGCAC AGTATTATCA GTTAATAAGA CTTGGCTTTG   1020
AGGGTTATAA GAACGTCATG AAGAATTGCT TATCAAACGC AAAAGTACTA ACAGAGGGAA   1080
TCACAAAAAT GGGGCGGTTC GATATTGTCT CTAAGGATGT GGGTGTTCCT GTTGTAGCAT   1140
TTTCTCTCAG GGACAGCAGC AAATATACGG TATTTGAAGT ATCTGAGCAT CTCAGAAGAT   1200
TTGGATGGAT CGTCCCTGCA TACACAATGC CACCGGATGC TGAACACATT GCTGTACTGC   1260
GGGTTGTCAT TAGAGAGGAT TTCAGCCACA GCCTAGCTGA GAGACTTGTT TCTGACATTG   1320
AGAAAATTCT GTCAGAGTTG GACACACAGC CTCCTCGTTT GCCCACCAAA GCTGTCCGTG   1380
TCACTGCTGA GGAAGTGCGT GATGACAAGG GTGATGGGCT TCATCATTTT CACATGGATA   1440
CTGTAGAGAC TCAGAAAGAC ATTATCAAAC ATTGGAGGAA AATCGCAGGG AAGAAGACCA   1500
GCGGAGTCTG CTAGGTCTGG CCACACTTGT TATCTGGGCT CCGCTTCCAT CGCCATCCTG   1560
TAGTATGTAT TACGTGTGTT GTTTCCATCT TATGTAGTAG TTGGTACTGT AATCTGTGTA   1620
AATGCTTTCA TGATCTTGGC TCTGTATATG CTAAATAAGC ACTGCATTTC AAGTTCCTGG   1680
AAGTATTTAT GTATGAATCA ATCCGGGCAT AATTGGTAGA ATGCCCTCTC TGCGTCATCT   1740
TTGAATTTCA CGTGCAATAA TATTTGAAAT CTACACCTAT TAT                     1783
```

(2) INFORMATION FOR SEQ ID NO:9:

(i) SEQUENCE CHARACTERISTICS:
(A) LENGTH: 497 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: ERTR1

(xi) SEQUENCE DESCRIPTION: SEQ ID NO:9:

```
ATTATATATT CATAAAATAA GAAAATGAAA TGATGAATTT TTGCTTGTTG TAACTATTTT     60
```

```
AGCATTGTTC TAAGTGTAGC AAATGCACAA CAATGTGGAA GTCAAGCTGG TGGAGCTTTG    120

TGTGCCAATG GGTTATGTTG TAGTCAATAT GGCTATTGTG GCACTACTCC TGATTACTGT    180

GGACAGGGAT GCCAGAGTCA ATGCAACTAA ATTATGTCTT GTGTGTACGT TCTAGCTTGA    240

AGGCTATGAT AATAATAAGG TAATATATAT CCATGTGGTT GTGTGTTAAA ATATATAAAT    300

TTGTATTACT AGAATAAAGT GGGAACATGT ATGTACTGTG AGTTAATTCC ACAAGACCAA    360

GAATATAGTG TCTGGTCATG AACACTATAT ATGTACTAGT TTGTTTGTTT TCTATTTCAA    420

TGTGATGTTT ATTAAGAATG GTCAAAAACC ACTTAATAAA AATGTCCACT ATTTAAGTAA    480

AAAAAAAAAA AAAAAAA                                                   497
```

(2) INFORMATION FOR SEQ ID NO:10:

(i) SEQUENCE CHARACTERISTICS:
(A) LENGTH: 1224 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: ERTS2

(xi) SEQUENCE DESCRIPTION: SEQ ID NO:10:

```
GGAATTCGGC ACGAGGAAGA TGCAAACATG TCGAGGTGGA TGACAAGGTT GGTATGGAGA     60

AGAACGGAAA AAAGCTTGAT CAAGGTGGTA GTGCATCAGA TGGCTTTTCA GTACCATCAC    120

AGGAAAAGGC AATCACCATA GAGCAGCCTA CAGATACTAC CAACACGGAG GAATCAGAAA    180

CAATTGAGGT TCTGCAGGAG AAAATGCAAA ATGCAGTTGA CAGAGATATT GAAATCCTTG    240

ATTCAGGAAA ACCAGTAGAA CAATCGCTGG AACCTCAACT ATCCATTGGT ACCAATGATG    300

AAGCTCGGGA GTACAAGCAG AAAATGGGGG AGGGACATAA GGAGGTGCAA GGTGAGGAAT    360

TGCAAGCTTG CGATGATGTT GTCGTCTCTG ATCATGACAA TGAAGGAAAA GAGCATAATG    420

TGGTGGTCGA GCAGCGGCAT GTGGAGAACT TCGAGATCCA AGCGAATGAA CCAGTAACTG    480

CCTATAATGC AGCACCTGTG ATCCAGGAAC CGGTGGATGG AAGTAAAGCT ATTGCCACTC    540

CAACGTCAGA AGCTGCAACT ACCGAGACAG AGATGTCAAG GGAGAAAGAA CTCGGTCTAG    600

CAGATGACCA CAACATACAT CCATCGATGT GTGTTGCCGG GGAAGTTAAT CCTGCTGATG    660

CTTCCCATTC TTTTGGTTCT ACGCCTATTG AAGTCCCAGG TAAGAATGCA AATGAGCTTA    720

AGGAATGGAA GAAAATGGAC ATGTTACCGG CATCGCCTAC TGCCAGCCAA GTATCCTGTG    780

ATAGTGATGC CCTGTCTGAA AGCAACAGAA AAATTATAGA GGAGAATGAA AAATTAAGGG    840

AGATGATGGA GAAGTTAATC AAATCAGGGA ACGAACAGCT GAGTGCCATA TCGAGTCTTT    900

CTGGAAGAGT TAAAGAGCTG GAGAAGAGAT TGTCCAAGAA GAAGAAGCTA AAATTGAAAC    960

GAAATAGGGT ACCAGCAGCT GGATCAGCCT GTGTAAAGCC ATTGAATGAC TCACTTAGAA   1020

ATAGGAATGT GGGTTGGCAA TGTAAAACAA AAGCTTGGTC ATTCCTTTCA TAGAATAGTA   1080

ATTTGGTTCA TGTGGTCTGT TTGCGTTCCA TTGTATGCTA TGTATAAATA AGGCTTCTTC   1140

TGCTCAGTTG TTGTTCCTTG CAATAGCTAC TTTGAAATTA CTTTGTTTGG CACCGAGGCT   1200

GACAATAACA ACGAACTTCA AAAA                                          1224
```

DNA ENCODING FRUIT-RIPENING-RELATED PROTEINS, DNA CONSTRUCTS, CELLS AND PLANTS DERIVED THEREFROM

This application relates to novel DNA constructs, plant cells containing the constructs and plants derived therefrom. In particular it involves the use of antisense or sense RNA technology to control gene expression in plants.

The modification of plant gene expression has been achieved by several methods. The molecular biologist can choose from a range of known methods to decrease or increase gene expression or to alter the spatial or temporal expression of a particular gene. For example, the expression of either specific antisense RNA or partial sense RNA has been utilised to reduce the expression of various target genes in plants (as reviewed by Bird and Ray, 1991, Biotechnology and Genetic Engineering Reviews 9:207–227). These techniques involve the incorporation into the genome of the plant of a synthetic gene designed to express either antisense or sense RNA. They have been successfully used to down-regulate the expression of a range of individual genes involved in the development and ripening of tomato fruit (Gray et al, 1992, Plant Molecular Biology, 19:69–87). Methods to increase the expression of a target gene have also been developed. For example, additional genes designed to express RNA containing the complete coding region of the target gene may be incorporated into the genome of the plant to "over-express" the gene product. Various other methods to modify gene expression are known; for example, the use of alternative regulatory sequences.

In work leading to the present invention, we have identified genes which encode proteins involved in ripening-related processes and which show novel expression patterns in normal and ripening inhibitor (rin) mutant tomatoes. DNA sequences encoding these proteins have been cloned and characterised. The DNA sequences may be used to modify plant characteristics, particularly the ripening characteristics of fruit, including tomatoes. The sequences in question are encoded (almost completely) in the following clones: ERXT1b, ERT10, ERT13, ER14, ERT15, ERT16b, ERT17, ERTD1, ERTR1 and ERTS2 (herein referred to as the "ERT clones" or "ERT sequences"). The clones were isolated as part of a research programme to identify genes expressed at the onset of tomato fruit ripening (Picton et al, 1993, Plant Molecular Biology, in press).

BACKGROUND TO THE ISOLATION OF THE ERT CLONES

Considering the large number of complex pathways involved in the fruit ripening process, and despite construction and screening of many tomato fruit cDNA libraries in the past decade, surprisingly few fruit- or ripening-specific genes and their functions have been identified. In order to address this specific area a new cDNA library was constructed (pERT clone series, Early Ripening Tomato) from the pericarp of a very early ripening stage of wild-type tomato fruit and differentially screened against mRNA obtained from the pericarp of ripening inhibitor (rin) mutant fruit of a similar developmental stage.

The rin mutation, first reported in 1968, is recessive, maps to chromosome 5 and is closely linked to the macrocalyx locus. It has pleiotropic effects on ripening, resulting in an extremely retarded ripening phenotype. Fruit demonstrate an increased resistance to many common post harvest pathogens and have been maintained for years without further signs of normal ripening or deterioration. Following extensive storage of fruit seeds may germinate and grow precociously within the fruit. Other aspects of plant growth and early fruit development appear unaffected by the rin mutation. However, the rin fruit fail to attain a normal level of pigmentation as a result of decreased accumulation of carotenoids, particularly lycopene, and there is a decreased rate of chlorophyll loss so that rin fruit remain green when wild-type fruit are fully red. The rin fruit eventually "ripen" to a lemon yellow colour after several weeks. These mutant fruit also fail to achieve normal flavour or aroma which has been correlated with the reduced production of a number of aromatic compounds.

Despite these considerable shortfalls the rin mutation is used in the heterozygous state in commercial tomato production, as in such a genetic state the deficiencies of the homozygous rin mutation regarding fruit quality are at least partially overcome. The major benefit of rin heterozygous tomatoes is the maintained firmness which gives the tomato improved handling characteristics particularly for fresh market applications.

Examination of total proteins of wild-type and rin pericarp reveals differences during ripening, some proteins being more abundant and others reduced in the mutant fruit as compared to wild-type. In vitro translation profiles suggest that such changes are the result of altered gene expression in the mutant fruit. Subsequent analysis with ripening-related cDNA clones showed altered patterns of accumulation of several mRNAs in the mutant fruit, suggesting that the rin mutation effects expression of many ripening-related genes.

At the onset of ripening, rin fruit do not show the autocatalytic rise in ethylene evolution characteristic of normal tomato fruit and ripen essentially as non-climacteric fruit. Therefore, it has been suggested that the rin mutation may affect ethylene receptors end thus lead to the retarded ripening phenotype. However, there is evidence that rin fruit are able to perceive ethylene but ethylene alone is unable to reverse the mutant phenotype. Application of high levels of exogenous ethylene does induce red pigmentation in rin fruit and leads to an increase in respiration rate but fails to induce autocatalytic ethylene production. Ethylene treatment also restores accumulation of some ripening-related mRNAs which are substantially reduced in the mutant fruits namely those homologous to PTOM 5 (phytoene synthase), pTOM 13 (ethylene-forming enzyme), pTOM 99 (now known to be encoded by the ethylene responsive gene E8) and E4, but fails to significantly increase accumulation of polygalacturonase (pTOM 6) mRNA.

rin fruit, as a non-climacteric background, have been used to examine transcriptional activation and accumulation of a number of ethylene-responsive genes. These experiments indicate that rin effects both transcriptional and post-transcriptional events. Transcription of both polygalacturonase and E4 genes, and thus subsequent mRNA accumulation, are effectively abolished in rin fruit. In contrast, transcription of the E8 (pTOM 99) and J49 genes is reduced and their homologous mRNAs accumulate at a reduced level. In the case of the E17 gene, the rin mutation appears to have no effect on transcription, but mRNA accumulation is severely impaired.

In view of the extreme nature of the rin ripening mutant and its diverse effects at the molecular level, where it affects the expression of many ripening-related genes, it is not an ideal breeding tool. However due to the nature of the mutation, we decided to use rin fruit mRNN as a probe to isolate fruit ripening-related cDNAs. A cDNA library produced from mRNA isolated from the pericarp of wild-type tomato fruit (*Lycopersicon esculentum* Mill. cv Ailsa Craig) at the first visible sign of fruit ripening was differentially screened to identify clones whose homologous mRNAs were present at various levels in fruit of the tomato ripening mutant, ripening inhibitor (rin). We have now isolated, characterized and sequenced a series of new cDNA clones whose homologous mRNAs show altered patterns of expression in rin fruit during ripening.

SUMMARY OF THE INVENTION

DNA CONSTRUCTS, CELLS AND PLANTS ACCORDING TO THE INVENTION

According to the present invention we provide a DNA construct comprising a DNA sequence as encoded by an ERT clone selected from the group comprising ERT1b, ERT10, ERT13, ERT14 ERT15, ERT16b, ERT17, ERTD1, ERTR1 and ERTS2 or as obtainable by the use of said clone as a hybridization probe. The DNA sequence may be derived from cDNA, from genomic DNA or synthetic polynucleotides (synthesised ab initio).

cDNA clones encoding the ERT sequences were deposited at The National Collections of Industrial and Marine Bacteria (23 St Machar Drive, Aberdeen, Scotland, AB2 1RY) under the terms of the Budapest Treaty on the dates and under the accession (NCIMB) numbers indicated below.

The base sequence of ERT1b (deposited on Mar. 18, 1993 as NCIMB 40544) is set out in SEQ ID NO 1.

The base sequence of ERT10 (deposited on Mar. 18, 1993 as NCIMB 40545) is set out in SEQ ID NO 2.

The base sequence of ERT13 (deposited on Mar. 18, 1993 as NCIMB 40546) is set out in SEQ ID NO 3.

The base sequence of ERT14 (deposited on Mar. 18, 1993 as NCIMB 40547) is set out in SEQ ID NO 4.

The base sequence of ERT15 (deposited on Mar. 18, 1993 as NCIMB 40548) is set out in SEQ ID NO 5.

The base sequence of ERT16b (deposited on Mar. 18, 1993 as NCIMB 40549) is set out in SEQ ID NO 6.

The base sequence of ERT17 (deposited on Jul. 5, 1993 as NCIMB 40569) is set out in SEQ ID NO 7.

The base sequence of ERTD1 (deposited on Sep. 30, 1993 and Dec. 9, 1993 as NCIMD 40588) is set out in SEO ID NO 8.

The base sequence of ERTR1 (deposited on Mar. 18, 1993 as NCIMB 40550) is set out in SEQ ID NO 9.

The base sequence of ERTS2 (deposited on Mar. 18, 1993 as NCIMB 40551) is set out in SEQ ID NO 10.

The ERT cDNA sequences have been inserted into plasmids for replication purposes (designated pERT1b, etc) within an *E coli* host.

cDNA clones encoding the ERT ripening-related proteins/enzymes may also be obtained from the mRNA of tomatoes or other plants by known screening methods similar to that described by Slater et al (1985, Plant Molecular Biology, 5:137–147) using suitable probes derived from one of the sequences shown as SEQ ID NO 1 to SEQ ID NO 10. Sequences coding for the wholes or substantially the whole of the mRNA produced by the ERT gene or genes may thus be isolated.

An alternative source of the ERT DNA sequence is a suitable gene encoding the particular ERT protein. This gene may differ from the cDNA in that introns may be present. The introns are not transcribed into mRNA (or, if so transcribed, are subsequently cut out). Oligonucleotide probes or the cDNA clone may be used to isolate the actual ERT gene(s) by screening genomic DNA libraries. A series of genomic DNA clones has already been isolated from tomato (*Lycopersicon esculentum*) by hybridisation to ERT cDNAs. Three of these genomic clones have been deposited at The National Collections of Industrial and marine Bacteria (23 St Machar Drives Aberdeen, scotland, AB2 1RY) under the terms of the Budapest Treaty:

ERT1 (geaomic DNA related to pERT1b) was deposited on Dec. 24, 1993 under the accession number NCIMB 40606;

ERT10 (genomic DNA related to pERT10) was deposited on Dec. 24, 1993 under the accession number NCIMB 40607;

ERT15 (genomic DNA related to pERT15) was deposited on Dec. 24, 1993 under the accession number NCIMB 40608.

The ERT genomic sequences have been inserted into λ bacteriophage ENBL3 for replication purposes (designated gERT1, gERT10, gERT15) using *E coli* K803 plating cells.

Such genamic DNA sequences may also be used as sources of gene promoters (transcriptional initiation sequences). The genomic clones may include control sequences operating in the plant genome. Thus it is also possible to isolate promoter sequences which may be used to drive expression of the ERT protein or any other protein. These promoters may be particularly responsive to ripening-related events and conditions. An ERT-gene promoter may be used to drive expression of any target gene.

A further way of obtaining an ERT DNA sequence is to synthesise it ab initio from the appropriate bases, for example using any one of SEQ ID NO 1 to SEQ ID NO 10 as a guide.

DNA sequences encoding the ERT ripening-related proteins or enzymes may be isolated not only from tomato but from any suitable plant species. Alternative sources of suitable genes may include bacteria, yeasts lower and higher eukaryotes.

The ERT sequences may be incorporated into DNA constructs suitable for plant transformation. These DNA constructs may then be used to modify ERT gene expression in plants. "Antisense" or "partial sense" or other techniques may be used to reduce the expression of the ERT protein(s) in developing and ripening fruit. The levels of the ERT proteins(s) may also be increased; for example, by incorporation of additional ERT sequence(s). The additional sequencers) may be designed to give either the same or different spatial and temporal patterns of expression in the fruit. The overall level of ERT gene activity and the relative activities of the individual ERT proteins/enzymes affect plant (notably fruit) development and thus determine certain characteristics of the plant/fruit. Modification of ERT protein/enzyme activity can therefore be used to modify various aspects of plant or fruit quality when compared to similar unmodified plants or fruit at a corresponding development stage.

The invention further provides a DNA construct comprising a DNA sequence as encoded by an ERT clone selected from the group consisting of ERT1b, ERT10, ERT13, ERT14, ERT15, ERT16b, ERT17, ERTD1, ERTR1 and ERTS2 or as obtainable by the use of said clone as a hybridization probe, in which said DNA sequence is under the control of a transcriptional initiation region operative in plants, so that the construct can generate RNA in plant cells. Such a DNA construct may be an "antisense" construct generating "antisense" RNA or a "sense" construct (encoding at least part of the functional ERT protein) generating "sense"RNA. "Antisense RNA" is an RNA sequence which is complementary to a sequence of bases in the corresponding mRNA: complementary in the sense that each base (or the majority of bases) in the antisense sequence (read in the 3' to 5' sense) is capable of pairing with the corresponding base (G with C, A with U) in the mRNA sequence read in the 5' to 3' sense. Such antisense RNA may be produced in the cell by transformation with an appropriate DNA construct arranged to generate a transcript with at least part of its sequence complementary to at least part of the coding strand of the relevant gene (or of a DNA sequence showing substantial homology therewith). "Sense RNA" is an RNA sequence which is substantially homologous to at least part of the corresponding mRNA sequence. Such sense RNA may be produced in the cell by transformation with an appropriate DNA construct arranged in the normal orientation so as to generate a transcript with a sequence identical to at least part of the coding strand of the relevant gene (or of a DNA sequence showing substantial homology therewith). Suitable sense constructs may be used to inhibit gene expression (as described in International Patent Publication W091/08299) or to over-express the protein/enzyme.

The transcriptional initiation region may be derived from any plant-operative promoter. The transcriptional initiation region may be positioned for transcription of a DNA sequence encoding RNA which is complementary to a substantial run of bases in a mRNA encoding a protein produced by an ERT gene (mating the DNA construct a full or partial antisense construct).

The characteristics of plant parts, particularly fruit, may be modified by transformation with a DNA construct according to the invention. The invention also provides plant cells containing such constructs, plants derived therefrom showing modified ripening characteristics; and seeds of such plants.

DESCRIPTION OF PREFERRED EMBODIMENTS

Figure 1:
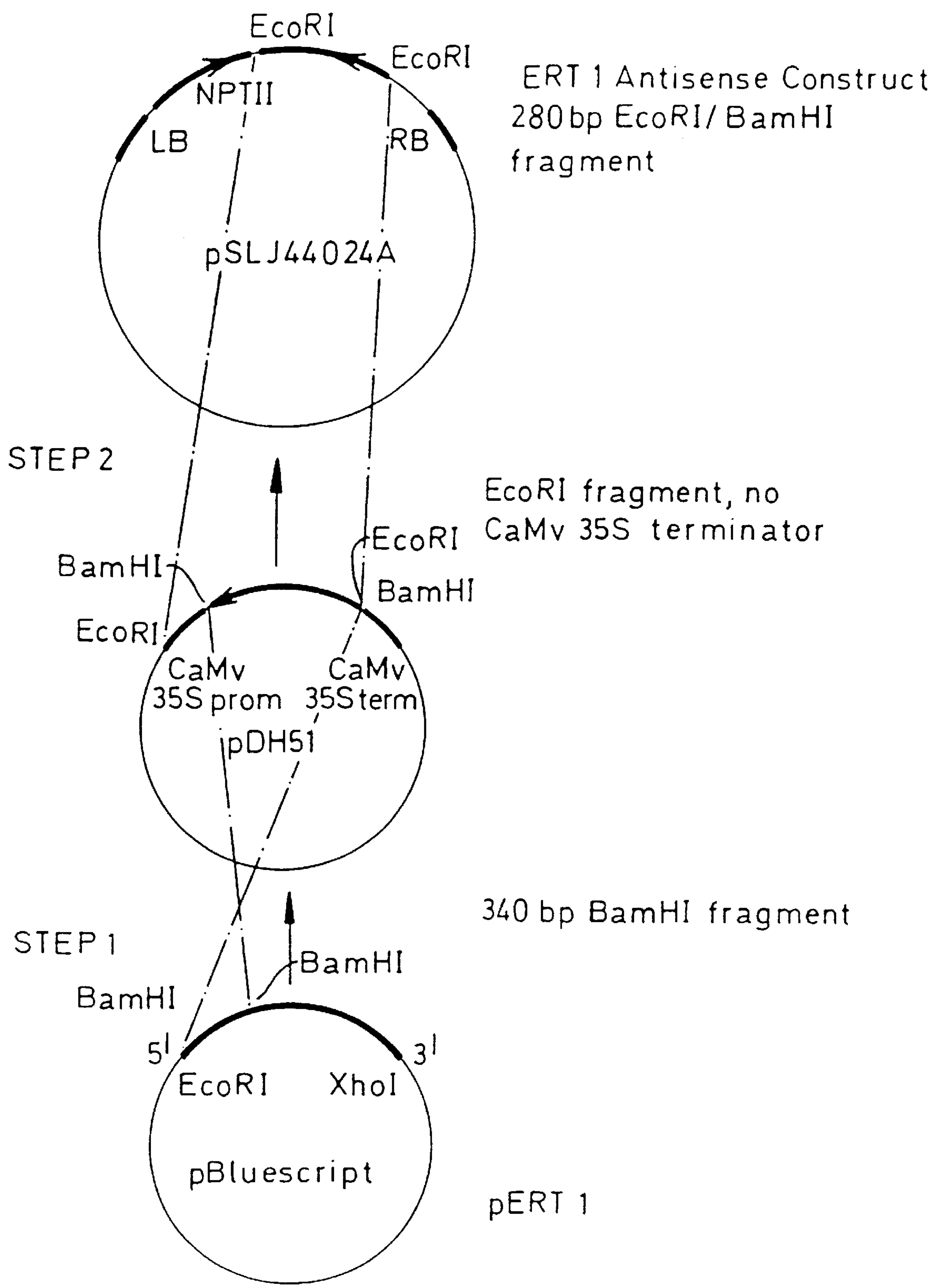
FIG. 1 is a diagram showing the construction of an ERT1 antisense construct without the CaMV 35S 3' end.

The constructs of the invention may be inserted into plants to regulate the production of proteins encoded by genes homologous to the ripening-related ERT clone. The constructs may be transformed into any dicotyledonous or monocotyledonous plant. Depending on the nature of the construct, the production of the protein may be increased, or reduced, either throughout or at particular stages in the life of the plant. Generally, as would be expected, production of the protein is enhanced only by constructs which express RNA homologous to the substantially complete endogenous ERT mRNA. Constructs containing an incomplete DNA sequence shorter than that corresponding to the complete gene generally inhibit the expression of the gene and production of the proteins, whether they are arranged to express sense or antisense RNA. Full-length antisense constructs also inhibit gene expression.

The plants to which the present invention can be applied include commercially important fruit-bearing plants, in particular tomato. In this way, plants can be generated which, amongst other phenotypic modifications, may have one or more of the following fruit characteristics:

improved resistance to damage during harvest, packaging and transportation due to slowing of the ripening and over-ripening processes;

longer shelf life and better storage characteristics due to reduced activity of degradative pathways (e.g. cell wall hydrolysis);

improved processing characteristics due to changed activity of proteins/enzymes contributing to factors such as: viscosity, solids, pH, elasticity;

improved flavour and aroma at the point of sale due to modification of the sugar/acid balance and other flavour and aroma components responsible for characteristics of the ripe fruit;

modified colour due to changes in activity of enzymes involved in the pathways of pigment biosynthesis (e.g. lycopene b-carotenee chalcones and anthocyanins);

increased resistance to post-harvest pathogens such as fungi.

The activity of the ERT protein may be either increased or reduced depending on the characteristics desired for the modified plant part (fruit leaf, flower, etc). The levels of ERT protein may be increased; for example, by incorporation of additional ERT genes. The additional genes may be designed to give either the same or different spatial and temporal patterns of expression in the fruit. "Antisense" or "partial sense" or other techniques may be used to reduce the expression of ERT protein.

The activity of each ERT protein or enzyme may be modified either individually or in combination with modification of the activity of one or more other ERT proteins/enzymes. In addition, the activities of the ERT proteins/enzymes may be modified in combination with modification of the activity of other enzymes involved in fruit ripening or related processes.

DNA constructs according to the invention may comprise a base sequence at least 10 bases (preferably at least 35 bases) in length for transcription into RNA. There is no theoretical upper limit to the base sequence—it may be as long as the relevant mRNA produced by the cell—but for convenience it will generally be found suitable to use sequences between 100 and 1000 bases in length. The preparation of such constructs is described in more detail below.

As a source of the DNA base sequence for transcription, a suitable cDNA or genomic DNA or synthetic polynucleotide may be used. The isolation of suitable ERT sequences is described above; it is convenient to use DNA sequences derived from the ERT clones deposited at NCIMB in Aberdeen. Sequences coding for the whole, or substantially the whole, of the appropriate ERT protein may thus be obtained. Suitable lengths of this DNA sequence may be cut out for use by means of restriction enzymes. When using genomic DNA as the source of a base sequence for transcription it is possible to use either intron or exon regions or a combination of both.

To obtain constructs suitable for expression of the appropriate ERT-related sequence in plant cells, the cDNA sequence as found in one of the pERT plasmids or the gene sequence as found in the gERT vectors or the chromosome of the plant may be used. Recombinant DNA constructs may be made using standard techniques. For example, the DNA sequence for transcription may be obtained by treating a vector containing said sequence with restriction enzymes to cut out the appropriate segment. The DNA sequence for transcription may also be generated by annealing and ligating synthetic oligonucleotides or by using synthetic oligonucleotides in a polymerase chain reaction (PCR) to give suitable restriction sites at each end. The DNA sequence is then cloned into a vector containing upstream promoter and downstream terminator sequences. If antisense DNA is required, the cloning is carried out so that the cut DNA sequence is inverted with respect to its orientation in the strand from which it was cut.

In a construct expressing antisense RNA, the strand that was formerly the template strand becomes the coding strand, and vice versa. The construct will thus encode RNA in a base sequence which is complementary to part or all of the sequence of the ERT-protein-encoding mRNA. Thus the two RNA strands are complementary not only in their base sequence but also in their orientations (5' to 3').

In a construct expressing sense RNA, the template and coding strands retain the assignments and orientations of the original plant gene. Constructs expressing sense RNA encode RNA with a base sequence which is homologous to part or all of the sequence of the mRNA. In constructs which express the functional ERT protein, the whole of the coding region of the gene is linked to transcriptional control sequences capable of expression in plants.

For example, constructs according to the present invention may be made as follows. A suitable vector containing the desired base sequence for transcription (such as a pERT or gERT vector) is treated with restriction enzymes to cut the sequence out. The DNA strand so obtained is cloned (if desired, in reverse orientation) into a second vector containing the desired promoter sequence and the desired terminator sequence. Suitable promoters include the 35S cauliflower mosaic virus promoter and the tomato polygalacturonase gene promoter sequence (Bird et ale 1988, Plant Molecular Biology, 11:651–662) or other developmentally regulated fruit promoters. Suitable terminator sequences include that of the *Agrobacterium tumefaciens* nopaline synthase gene (the nos 3'end).

The transcriptional initiation region (or promoter) operative in plants may be a constitutive promoter (such as the 35S cauliflower mosaic virus promoter) or an inducible or developmentally regulated promoter (such as fruit-specific promoters), as circumstances require. For example, it may be desirable to modify ERT protein activity only during fruit development and/or ripening. Use of a constitutive promoter will tend to affect ERT protein levels and functions in all parts of the plant, while use of a tissue specific promoter allows more selective control of gene expression and affected functions. Thus in applying the invention (for example, to tomatoes) it may be found convenient to use a promoter that will give expression during fruit development and/or ripening. Thus the antisense or sense RNA is produced only in the organ in which its action is required and/or only at the time required. Fruit development and/or ripening-specific promoters that could be used include the ripening-enhanced polygacturonase promoter (International Patent Publication Number W092/08798), the E8 promoter (Diekman & Fischer, 1988, EMBO, 7:3315–3320), the fruit specific 2A11 promoter (Pear et al, 1989, Plant Molecular Biology, 13:639–651), the histidine decarboxylase promoter (HDC, Sibia) and the phytoene synthase promoter.

ERT protein or enzyme activity (and hence ripeing-related processes and fruit ripening characteristics) may be modified to a greater or lesser extent by controlling the degree of the appropriate ERT protein's sense or antisense mRNA production in the plant cells. This may be done by suitable choice of promoter sequences, or by selecting the number of copies or the site of integration of the DNA sequences that are introduced into the plant genome. For example, the DNA construct may include more than one DNA sequence encoding the ERT protein or more than one recombinant construct may be transformed into each plant cell.

The activity of each ERT protein may be separately modified by transformation with a suitable DNA construct comprising an ERT sequence In addition, the activity of two or more ERT proteins may be simultaneously modified by transforming a cell with two or more separate constructs the first comprising a first ERT sequence (such as ERT1b) and the second (or further) comprising a second ERT sequence (such as ERT10 and/or ERT13, etc). Alternatively, a plant cell may be transformed with a single DNA construct comprising both a first ERT sequence and a second ERT sequence.

It is also possible to modify the activity of the ERT protein(s) while also modifying the activity of one or more other enzymes. The other enzymes may be involved in cell metabolism or in fruit development and ripening. Cell wall metabolising enzymes that may be modified in combination with an ERT protein include but are not limited to: pectin esterase, polygalacturonase, β-galactanase, β-glucanase. Other enzymes involved in fruit development and ripening that may be modified in combination with an ERT protein include but are not limited to: ethylene biosynthetic enzymes, carotenoid biosynthetic enzymes including phytoene synthase, carbohydrate metabolism enzymes including invertase.

Several methods are available for modification of the activity of the ERT protein(s) in combination with other enzymes. For example, a first plant may be individually transformed with an ERT construct and then crossed with a second plant which has been individually transformed with a construct encoding another enzyme. As a further example, plants may be either consecutively or co-transformed with ERT constructs and with appropriate constructs for modification of the activity of the other enzyme(s). An alternative example is plant transformation with an ERT construct which itself contains an additional gene for modification of the activity of the other enzyme(s). The ERT constructs may contain sequences of DNA for regulation of the expression of the other enzyme(s) located adjacent to the ERT sequences. These additional sequences may be in either sense or antisense orientation as described in international patent application publication number W093/23551 (single construct having distinct DNA regions homologous to different target genes). By using such methods, the benefits of modifying the activity of the ERT proteins may be combined with the benefits of modifying the activity of other enzymes.

A DNA construct of the invention is transformed into a target plant cell. The target plant cell may be part of a whole plant or may be an isolated cell or part of a tissue which may be regenerated into a whole plant. The target plant cell may be selected from any monocotyledonous or dicotyledonous plant species. Suitable plants include any fruit-bearing plant (such as tomatoes, mangoes, peaches, apples, pears, strawberries, bananas, melons). For any particular plant cell, the ERT sequence used in the transformation construct may be derived from the same plant species, or may be derived from any other plant species (as there will be sufficient sequence similarity to allow modification of related isoenzyme gene expression).

Constructs according to the invention may be used to transform any plant using any suitable transformation technique to make plants according to the invention. Both monocotyledonous and dicotyledonous plant cells may be transformed in various ways known to the art. In many cases such plant cells (particularly when they age cells of dicotyledonous plants) may be cultured to regenerate whole plants which subsequently reproduce to give successive generations of genetically modified plants. Any suitable method of plant transformation may be used. For example, dicotyledonous plants such as tomato and melon may be transformed by Agrobacterium Ti plasmid technology, such as described by Bevan (1984, Nucleic Acid Research, 12:8711–8721) or Fillatti et al (Biotechnology, July 1987, 5:726–730) Such transformed plants may be reproduced sexually, or by cell or tissue culture.

Transgenic plants and their progeny may be used in standard breeding programmes, resulting in improved plant lines having the desired characteristics. For example, fruit-bearing plants expressing an ERT construct according to the invention may be incorporated into a breeding programme to alter fruit-ripening characteristics and/or fruit quality. Such altered fruit may be easily derived from elite lines which already possess a range of advantageous traits after a substantial breeding programme: these elite lines may be further improved by modifying the expression of a single targeted ERT protein/enzyme to give the fruit a specific desired property.

By transforming plants with DNA constructs according to the invention, it is possible to produce plants having an altered (increased or reduced) level of expression of one or more ERT proteins, resulting from the presence in the plant genome of DNA capable of generating sense or antisense RNA homologous or complementary to the RNA that generates such ERT proteins. For fruit-bearing plants, fruit may be obtained by growing and cropping using conventional methods. Seeds may be obtained from such fruit by conventional methods (for example, tomato seeds are separated from the pulp of the ripe fruit and dried, following which they may be stored for one or more seasons). Fertile seed derived from the genetically modified fruit may be grown to produce further similar modified plants and fruit.

The fruit derived from genetically modified plants and their progeny may be sold for immediate consumption, raw or cooked, or processed by canning or conversion to soup, sauce or paste. Equally, they may be used to provide seeds according to the invention.

The genetically modified plants (transformed plants and their progeny) may be heterozygous for the ERT DNA constructs. The seeds obtained from self fertilisation of such plants are a population in which the DNA constructs behave like single Mendelian genes and are distributed according to Mendelian principles: eg, where such a plant contains only one copy of the construct, 25% of the seeds contain two copies of the construct, 50% contain one copy and 25% contain no copy at all. Thus not all the offspring of selfed plants produce fruit and seeds according to the present invention, and those which do may themselves be either heterozygous or homoaygous fog the defining trait. It is convenient to maintain a stock of seed which is homozygous for the ERT DNA construct. All crosses of such seed stock will contain at least one copy of the construct, and self-fertilized progeny will contain two copies, i.e. be homozygous in respect of the character. Such homozygous seed stock may be conventionally used as one parent in F1 crosses to produce heterozygous seed for marketing. Such seed, and fruit derived from it, form further aspects of our invention. We further provide a method of producing F1 hybrid plants expressing an ERT DNA sequence which comprises crossing two parent lines, at least one of which is homozygous for an ERT DNA construct. A process of producing F1 hybrid seed comprises producing a plant capable of bearing genetically modified fruit homozygous for an ERT DNA construct, crossing such a plant with a second homozygous variety, and recovering F1 hybrid seed. It is possible according to our invention to transform two or more plants with different ERT DNA constructs and to cross the progeny of the resulting lines, so as to obtain seed of plants which contain two or more constructs leading to reduced expression of two or more fruit-ripening-related ERT proteins.

The invention is also described with reference to the SEQUENCE LISTING in which:

SEQ ID NO 1 shows the base sequence of the cDNA clone ERT1b.

SEQ ID NO 2 shows the base sequence of the cDNA clone ERT10.

SEQ ID NO 3 shows the base sequence of the cDNA clone ERT13.

SEQ ID NO 4 shows the base sequence of the cDNA clone ERT14.

SEQ ID NO 5 shows the base sequence of the cDNA clone ERT15.

SEQ ID NO 6 shows the base sequence of the cDNA clone ERT16b.

SEQ ID NO 7 shows the base sequence of the cDNA clone ERT17.

SEQ ID NO 8 shows the base sequence of the cDNA clone ERTD1.

SEQ ID NO 9 shows the base sequence of the cDNA clone ERTR1.

SEQ ID NO 10 shows the base sequence of the cDNA clone ERTS2.

The following Examples illustrate aspects of the invention.

EXAMPLE 1

Construction of a tomato wild-type ripening fruit cDNA library.

Tomato plants (*Lycopersicon esculentum* Mill. cv Ailsa Craig, +/+ and rin/rin genotypes) were grown under standard conditions. Flowers were tagged at anthesis and fruit removed from the plant, at a very early-breaker stage, when changes in pigmentation of the fruit were first apparent. This stage corresponded to 43 to 48 days post-anthesis. Pericarp samples were frozen in liquid nitrogen and stored at −80° C. Total RNA was extracted from the pooled pericarp of approximately four fruit as has been previously described Poly(A)$^+$ mRNA was isolated by oligo dT Cellulose chromatography using a POLY(A)QUIK mRNA purification kit according to the manufacturers protocol (Stratagene, Calif., USA). Following two passages through the column, RNA was quantified spectrophotometrically. Double stranded cDNA was synthesised from approximately 5 $\mu$g mRNA using a λ ZAP cDNA synthesis kit. cDNA was ligated into λ UNI-ZAP II, encapsidated in vitro and amplified immediately in *E coli* strain XZ1-Blue following the manufacturers instructions (Stratagenee Calif., USA).

EXAMPLE 2

Isolation of the pERT clones.

The wild-type tomato fruit cDNA library was estimated to represent >$10^6$ primary recombinants. Following a single amplification step, non-recombinants were estimated at less than 3% of the total recombinants. Insert size of cloned cDNAs, obtained following PCR of randomly selected clones using T3 and T7 oligonucleotide primers, was estimated to be between 500 bp and 2.2 Kb with a median of approximately 1.0 Kb. Approximately $5\times10^5$ primary recombinants were screened in aliquots of 30–50,000 pfus on 14 cm petri dishes. Duplicate plaque lifts were obtained from each plate using nylon membranes (Hybond N$^+$, Amersham PLC,UK). Differential hybridisation probes were obtained by reverse transcription of poly(A)$^+$, mRNA isolated from very early-breaker wild-type or rin fruit as described above. Following differential screening of 30–500,000 pfuse 53 potential positives showing reduced accumulation in the pericarp of early-breaker rin fruit were isolated, two clones showing a high level of accumulation in both wild-type and rin early-breaker fruit were identified and a further subset of 28 clones showed increased accumulation in the rin fruit. Following plaque purification and subsequent in vivo excision of the cloned inserts, 15 cDNAs continued to show reduced accumulation in rin fruit (the rin negative clones), a single clone showing high levels of accumulation in both wild-type and rin fruit (the early breaker, EB, clone) was identified and a further group of 14 clones showing increased accumulation in the pericarp of early-breaker rin fruit (the rin positive clones) were also obtained. This latter group of clones contains a family of 8 cross-hybridising cDNAs and 6 further unique clones.

The group of clones described as rin negative clones include ERT1b, ERT10, ERT13, ERT14 and ERT15.

The group of clones described as rin positive clones include ERT17, ERTD1, ERTR1 and ERTS2.

ERT16 is the clone which showed high levels of expression in both wild type and rin mutant fruit at early stages of ripening.

EXAMPLE 3

Characterisation of the ERT cDNA clones.

3.1 ERT1b 3.1 ERT1b homologous transcripts are 1.8 kb in size and it is only found expressed during ripening of the wild type fruit. It is not found in other organs of the tomato plant. It is expression is highest during early stages of fruit ripening (eg breaker plus 3). After this the levels of ERT1 mRNA decline. Levels of expression of this mRNA are low in rin mutant tomatoes and are restricted to ripening rin tomatoes. The gene is not activated upon wounding. The levels of mRNA homologous to ERT1 were increased by ethylene treatment of the mutant fruit.

Initial sequence analysis of ERT1 (1541 base pairs) indicated, by reference to the obtained transcript size, that the clone was not full length and the cDNA library was rescreened for a longer clone. A further clone, ERT1b was isolated and sequenced. ERT1b is totally homologous to ERT1 but is longer (1669 base pairs). Further attempts are being made to re-screen the library for a full length ERT1 cDNA.

The full DNA sequence and deduced amino acid sequence of ERT1b is shown in SEQ ID NO 1. The ERT1b sequence has been placed on the EMBL datase (accession number× 72729).

The ORF of ERT1b showed similarity to the amino acid sequence of UDP Flavonol-3-0-glucosyl transferase (EC 2.4.1.91) of maize (69% similarity, 26.3% identity over a region of 403 amino acids, accession numbers P16165-7) and barley (69.5% similarity, 27.1% identity over a region of 354 amino acids, accession number P14726), and UDP-glucuronosyl transferases (EC 2.4.1.17) of rat (64.9% similarity, 25% identity over a region of 232 amino acids, accession number P08430) and human (66.2% similarity, 30.7% identity over a region of 114 amino acids, accession number P19224). Homology has also been shown at the DNA level to a transcribed *A thaliana* sequence (clone YAP004T7) with homology to maize flavanol-3-0-glucosyl transferase (58.1% identity in a 279 bp overlap, accession number Z17579).

3.2 ERT10

ERT 10 homologous transcripts are 1.35 kb in size and it is only found expressed during ripening of the wild type fruit. It is not found in other organs of the tomato plant. It's expression is highest during early stages of fruit ripening (eg breaker plus 3) After this the levels of ERT10 mRNA decline. Levels of expression of this MRNA are low in rin mutant tomatoes and are restricted to ripening rin tomatoes. The gene is not activated upon wounding.

The sequence of pERT10 is shown in SEQ ID NO 2. The ERT10 sequence has been placed on the EMBL datase (accession number×72730).

An amino acid sequence derived from an ORF of ERT10 is a perfect match with the shortchain or "insect-type" alcohol dehydrogenase family signature (containing the tyrosine residue known to be involved in catalytic activity and/or subunit binding in some dehydrogenases)e however it shows an additional region of homology to glucose dehydrogenases.

3.3 ERT13

ERT13 homologous transcripts are 1.1 kb in size and it is only found expressed during ripening of the wild type fruit. It is not found in other organs of the tomato plant. It's expression increases during fruit development and is highest around breaker stage (eg breaker plus 3). After this the levels of ERT13 mRNA decline. Levels of expression of this mRNA are also high during the early stages of fruit development of rin fruit. ERT13 is also expressed in the leaf and in wounded leaf of rin tomatoes. The gene is not activated upon wounding. The levels of mRNA homologous to ERT13 were increased by ethylene treatment of the mutant fruit.

The sequence of ERT13 is shown in SEQ ID No 3. The ERT13 sequence has been placed on the EMBL datase (accession number×72731).

Searches in DNA sequence data bases have identified homology between the ERT13 cDNA sequence and the potato TUB8 cDNA sequence. TUB8 is a gene from *Solanum tuberosum* which is induced during the early stages of tuberisation in different organs of the potato plant (Taylor et ale 1992, Plant Molecular Biology, 20:641–651); a structural role is suggested for the encoded protein, which may be a stolon-tip protein.

3.4 ERT14

ERT14 homologous transcripts are 0.85 kb in size. It's expression is maximal at breaker plus one day with high levels of expression also detectable at breaker and in early fruit development stages. During fruit ripening the expression of ERT14 decreases. Expression is also detectable during fruit development of the rin fruit and in wounded and unwounded control and rin leaf. The levels of mRNA homologous to ERT14 were increased by ethylene treatment of the mutant fruit.

The sequence of ERT14 is shown in SEQ ID NO 4. The ERT14 sequence has been placed on the EMBL datase (accession number×72732).

Searches in DNA and protein sequence data bases do not identify any homologies.

3.5 ERT15

ERT15 homologous transcripts are 6.0 kb in size. It's expression is maximal at breaker plus one day with high levels of expression also detectable at breaker but not in early fruit development stages. During fruit ripening the expression of ERT15 decreases. In rin fruit expression is only detectable at the yellow colour stage. In wounded and unwounded control and rin leaf ERT15 expression is also detectable.

The sequence of ERT15 is shown in SEQ ID No 5. The ERT15 sequence has been placed on the EMBL datase (accession number×72734).

Searches in DNA and protein sequence data bases do not identify any homologies.

3.6 pERT16b

Using ERT16, the cDNA library was rescreened for a longer clone. A further clone, ERT16b was isolated and sequenced. The ERT16b transcript is estimated to be approximately 1.0 kb.

It has been shown that the mRNA for which ERT16b codes is expressed in the developing and ripening tomato fruit. ERT16b mRNA are easily detectable in immature green fruit and increase throughout fruit development reaching a peak of expression between breaker plus 5 to breaker plus seven days. The levels stay high even during late ripening stages.

In the rin mutant fruit the expression of ERT16b was similar to that of control tomaotes. In low ethylene tomatoes (eg low EFE tomatoes) levels of ERT16b mRNA were similar to levels found in unmodified tomato fruit at any of the ripening stages investigated On the other hand, ERT16b mRNA levels were not seen in leaves or wounded leaves of tomato.

The sequence of ERT16b is shown in SEQ ID NO 6. The ERT16b sequence has been placed on the EMBL datase (accession number×72733).

Searches of nucleotide sequence databases on the Daresbury SERC system (EMBL, GenBank) indicate the ERT16b sequence is homologous to the sequence of a cDNA derived from ripe tomato fruit pericarp. The associated transcript is induced by water stress in leaves and ripening in fruit (sequence submitted by N D Lussem D M Bartholomew and P A Scolnik; Accession Number L08255, TOKASRIP). The homology is 98.9% over 632 nucleotides (the full length of the ERT16b sequence)

3.7 ERT17

ERT17 mRNA is detected during fruit development and increases to a peak after the onset of ripening. It is present in leaves and at an increased level in senescing and mechanically wounded leaf tissue. Although ripening wounding and foliar senescence are all ethylene mediated processes ERT17 mRNA accumulation in fruit is not increased by ethylene treatment and thus its interrelationship with ethylene evolution appears casual not causal The terminal differentiation of these ripening, senescent, and wounded tissues suggests a possible role for this $E2_{16.5}$ enzyme in selective protein degradation that occurs during plant cell or organ senescence.

The three other plant E2s reported (Sullivan and Viestra, 1989, 1991) all show high homology with an E2 encoded by the *S cerevisiae* DNA repair gene, RAD6. The ERT17 sequence shows greatest homology with the yeast class I UBC4/UBC5 type E2 enzymes, implicated specifically in the ubiquitination and breakdown of very short-lived and abnormal proteins (Jentsch, 1992) and is the first E2 of this class to be identified from higher plants.

Both strands of the cDNA were sequenced by double-stranded miniprep plasmid DNA sequencing with Sequenase II (Synthetic oligonucleotides to the known sequence used as primers). The sequence of ERT17 is shown in SEQ ID NO 7. The complete cDNA and deduced amino acid sequences were compared with GenBank, DDJB and EMBL data bases. The ERT17 sequence has been placed on the EMBL datase (accession number×72719).

The characteristics of the cDNA were analysed. The 5' flanking region is 12 nucleotides long. The 3' un-translated region is 212 nucleotides long and is followed by 18 base pairs of poly(A) tail. There is no obvious polyadenylation signal sequence. The sequence has 77.7% identity in a 395 nt overlap with a *A thaliana* clone YAP 161T7 (Z17692), 71.2% identity in a 410 nt overlap with the yeast UBC5 gene (P15732), 78.5% identity in a 247 nt overlap with a *A thaliana* clone TAY050 (Z18473) and 70.7% identity in a 396 nt overlap with the yeast UBC4 gene (P15731).

The structural features of the deduced protein were also analysed. There is an open reading frame of 148 amino acids, giving a predicted molecular mass of protein 16.5 kD, pI 7.95. Comparisons with sequenced and deduced protein sequences using FASTA (Pearson, 1990, Methods Enzymol, 183g63–93) show strong homology with yeast UBC4 (78% identity, 95% similarity, P15731), and UBC5 (75% identity, 93% similarity, P15732) and the Drosophila UBC4 (78% identity, 89% similarity, P25867). There is also at least 33% identity (or 53% similarity) with a further 15 ubiquitin conjugating enzyme sequences from yeast (P06104, P21734, P23566, P14682, P28263, P29340), Drosophila (P25153), Arabidopsis (P25865), Triticum (P25866, P25868, P16577) and mammalian (P27924, P23567) and viral (P27949, P25869) sources. The deduced ERT17 protein contains the UBC putative active cysteine residue at position 85.

In summary, the clone ERT17 apparently encodes a tomato ubiquitin conjugating enzyme. ERT17 is homologous at both amino acid and DNA level to several published ubiquitin conjugating enzymes. Ubiquitin is a small, abundant protein present seemingly in all eukaryotic cells, which is covalently ligated to specific protein substrate's via an ATP dependent reaction. This ubiquitination has been demonstrated to target proteins for subsequent cellular degradation. Briefly, the process involves activation of ubiquitin, catalysed by ubiquitin-activating enzymes (E1s), transfer to a family of ubiquitin-carrier/ conjugating proteins with different substrate specificities (UBCs or E2s) and, finally, ubiquitin-protein ligation by either direct transfer of ubiquitin from E2 or mediated transfer utilising ubiquitin-protein ligases (E3s) (Hershko and Ciechanover, 1992, Ann Rev Biochem, 61:761–807; Jentsch, 1992, Ann Rev Genet, 26:179–207).

The clone ERT17 includes a full length tomato UBC cDNA ($E2_{16.5}$). The cloned mRNA encodes a derived 148 amino acid sequence of 16.5 kD with a pI of 7.95. The peptide has a conserved region containing a putative active cysteine residue at position 85 that is observed in other UBC or E2 sequences (Sullivan and Viestra, 1989a Proc Natl Acad Sci USA, 86:9861–9865; Jentsch et al, 1990, Trends Biochem Sci, 15:195–198) and thought to be required for the thiol ester formation with ubiquitin (van Nocker and Vierstra, 1991, Biochemistry, 88:10297–10301). In addition, a further cysteine residue is present at position 108. The presence of two cysteine residues and two ubiquitin thiol ester species has been observed for both wheat and Arabidoosis E2s, suggesting that the UBC may interact with more than a single ubiquitin simultaneously (Sullivan and Viestra, 1991, J Biol Chem, 266:23878–23885).

Modifying the expression of the ERT17-related gene may affect metabolic processes involving ubiquitin (such as the rate and manner of protein degradation) and consequently produce plants with an altered phenotype.

3.8 ERTD1

ERTD1 homologous transcripts are 1.8 kb in size.

The ERTD1 homologous transcript is found throughout early fruit development of both wild-type and rin fruit. It is also detected at early stages of ripening of wild-type fruit but then disappears. The transcript is detected throughout the entire ripening period in rin fruit. In other words, the transcript disappears during the early ripening of wild-type fruit but continues to be present throughout the ripening of rin fruit. The transcript is not detected in leaves or wounded leaves of either wild-type or rin.

The sequence of ERTD1 is shown in SEQ ID NO 8. The sequence contains a region identified as a glutamate decarboxylase.

3.9 ERTR1

ERTR1 homologous transcripts are 0.7 kb in size.

The ERTR1 homologous transcript is found throughout early fruit development of both wild-type and rin fruit. It is also detected at early stages of ripening of wild-type fruit but then disappears. The transcript is detected throughout the entire ripening period in rin fruit. In other words, the transcript disappears during the early ripening of wild-type fruit but continues to be present throughout the ripening of rin fruit. The transcript is not detected in leaves or wounded leaves of either wild-type or rin.

The sequence of ERTR1 is shown in SEQ ID NO 9. The sequence contains a region identified as a chitin binding site suggesting that this clone may be a fruit specific chitinase.

Upon recreening of the library, the longer clones ERTR1B1 and ERTR1C1 were found and the extended ERTR1 sequence was thus obtained. Stop codons at the beginning of the sequence are probably sequencing errors due to the poor resolution of the sequencing gels obtained for this region. The short region of the putative translation product which displays homology to plant chitinases is encoded from base number 89 to number 191, while the area containing the consensus chitin binding site is encoded from base number 95 to base number 180.

3.10 ERTS2

ERTS2 homologous transcripts are 4.7 kb in size and it is only found expressed during ripening of the rin fruit. It is present in wild type fruit but at a very low level.

The sequence of ERTS2 is shown in SEQ ID NO 10; it is not a full length clone but has an estimated transcript size of 4.5 Kb. Sequences searches in DNA and protein databases have not revealed any homology to known genes.

EXAMPLE 4

Characterisation of genaic ERT clones

Genomic clones corresponding to the ERT series of cDNA clones were identified as follows. A genomic library (ClonTech, Tomato variety VFN 8) was screened with the ERT clones using the entire cDNA insert as probe. Each clone was used as a screen against approximately 200,000 PFUs. All first round positives were cored and rescreened at lower density and, if needed, rescreened a third time to isolate plaque pure positives. The genomic clones are listed and described below.

4.1 gERT1 gERT1 is a genomic clone homologous to ERT1 cDNA and the 5' ERT1 PCR fragment.

The gene(s) is expressed in a highly fruit and ripening-specific manner, is not wound induced, is induced by ethylene treatment and present at only very low levels in rin tomatoes. Data suggests gERT1 represents a single gene. It appears to be a member of the ERT1 gene family, and is closely related to the gene expressing ERT1 mRMA. The associated promoters may have the same expression pattern.

4.2 gERT10.1 gERT10.1is a genoaic clone homologous to ERT10 cDNA and the 5' ERT10 PCR fragment.

Data (including southerns) suggests that the ERT10 gene is single copy. Expression is highly fruit and ripening-specific, not wound induced, not ethylene induced and present at very low levels in rin.

A second clone (gERT10.2) hybridises with the ERT10 cDNA and originally lit up with the 5' PCR fragment, but a first attempt to subclone from it was unsuccessful.

4.3 gERT13.1 gERT13.1 is a genomic clone homologous to ERT13 cDNA and the 5' ERT13 PCR fragment.

The gene appears to be single copy and is expressed throughout fruit development, shows a 50% rise during ripening, is not would induced but increases 50% with ethylene treatment. Its pattern of accumulation in rin does not show the rise during ripening. A similar DNA sequence has been obtained from potato stolon tips, so it may show expression in roots as well (but in a regulated manner).

A second clone, gERT13.2, was also detected.

4.4 gERT14 gERT14 is a genomic clone homologous to ERT14 cDNA and the 5' ERT14 PCR fragment.

The gene appears to be single copy and is expressed at substantial levels in both immature and mature fruit and also leaves. It shows a >50% rise during ripening of wild-type fruits but not rin. It is not would induced but increases dramatically following ethylene treatment.

4.5 gERT15 gERT15 is a genomic clone homologous to ERT15 cDNA and the 5' ERT15 PCR fragment.

The gene appears to be single copy. Its expression is highly fruit and ripening-specific. It is present at low levels in leaves and is not wound or ethylene induced.

4.6 gERT16 gERT16 is a genomic clone homologous to ERT16 cDNA and the 5' ERT16 PCR fragment.

This appears to be a multigene family. The gene(s) are active throughout fruit development and ripening and absent in leaves. The gene(s) are not induced by wounding but are induced by ethylene.

EXAMPLE 5

Construction of antisense RNA vectors with the CaMV 35S promoter.

A vector is constructed using sequences corresponding to a restriction fragment obtained from a pERT vector and is cloned into the vectors GA643 (An et al 1988, Plant molecular Biology Manual A3: 1–19) or pDH51 (Pietrzak et al, 1986, Nucleic Acids Research, 14:5875–5869) which has previously been cut with a compatible restriction enzyme(s). A restriction fragment from the pERT/pDH51 clone containing the promoter, the pERT fragment and other pDH51 sequence is cloned into SLJ44026B or SLJ44024B (Jones et al, 1990, Transgenic Research, 1) or a Bin19 (Bevan, 1984, Nucleic Acids Research, 12:8711–8721) which permits the expression of the antisense RNA under control of the CaMV 35S promoter.

After synthesis of the vector, the structure and orientation of the sequences are confirmed by DNA sequence analysis.

EXAMPLE 6

Construction of antisense RNA vectors with the polygalacturonass promoter.

The fragment of the pERT cDNA described in Example 5 is also cloned into the vector pJR3. pJR3 is a Bin19 based vector, which permits the expression of the antisense RNA under the control of the tomato polygalacturonase promoter. This vector includes approximately 5 kb of promoter sequence and 1.8 kb of 3' sequence from the PG promoter separated by a multiple cloning site.

After synthesis, vectors with the correct orientation of pERT sequence are identified by DNA sequence analysis.

EXAMPLE 7

Construction of truncated sense RNA vectors with the CaMV 35S promoter.

The fragment of pERT cDNA described in Example 5 is also cloned into the vectors described in Example 5 in the sense orientation.

After synthesis, the vectors with the sense orientation of pERT sequence are identified by DNA sequence analysis.

EXAMPLE 8

Construction of truncated sense RNA vectors with the polygalacturonase promoter.

The fragment of pERT cDNA that was described in Example 5 is also cloned into the vector pJR3 in the sense orientation.

After synthesis, the vectors with the sense orientation of pERT sequence are identified by DNA sequence analysis.

EXAMPLE 9

Construction of a pERT over-expression vector using the CaMV35S promoter.

The complete sequence of the pERT cDNA clone is inserted into the vectors described in Example 5.

EXAMPLE 10

Construction of a pERT over-expression vector using the polygalacturonase promoter.

The complete sequence of the pERT cDNA clone is inserted into pJR3.

EXAMPLE 11

Constructs made for plant transformation

FIG. 1 is a diagram showing the construction of an ERT1 antisense construct without the CaMV 35S 3' end (terminator). ERT1 is the cDNA clone which is 128 bases shorter than ERT1b. pERT1 was digested with BamHI and the resulting 340 base pair fragment was cloned into BamHI-cut pDH51. The EcoRI fragment (minus 60 base pairs of ERT1 sequence) was removed from this vector and ligated into EcoRI-cut pSLJ44024A.

Figure 2:
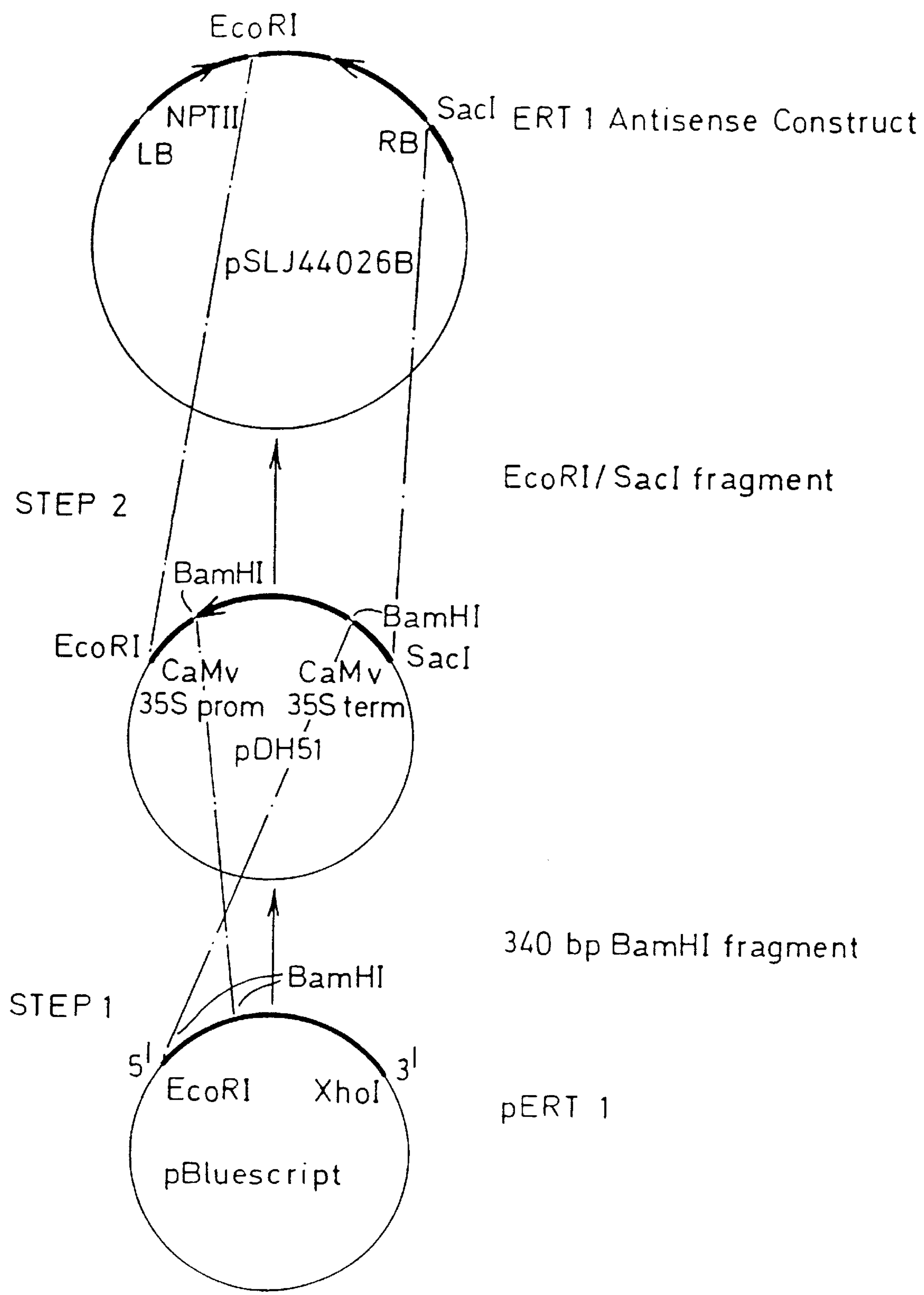
FIG. 2 is a diagram showing the construction of an ERT1 antisense construct with the CaMV 35S 3' end.

FIG. 2 is a diagram showing the construction of an ERT1 antisense construct with the CaMV 35S 3' end. pERT1 was digested with BamHI and the resulting 340 base pair fragment was cloned into BamHI-cut pDH51. Digestion with SacI, followed by partial digest with EcoRI, yielded a fragment with the CaMV 35S 3' end intact. This was ligated into EcoRI/SacI-cut pSLJ44026.

Figure 3:
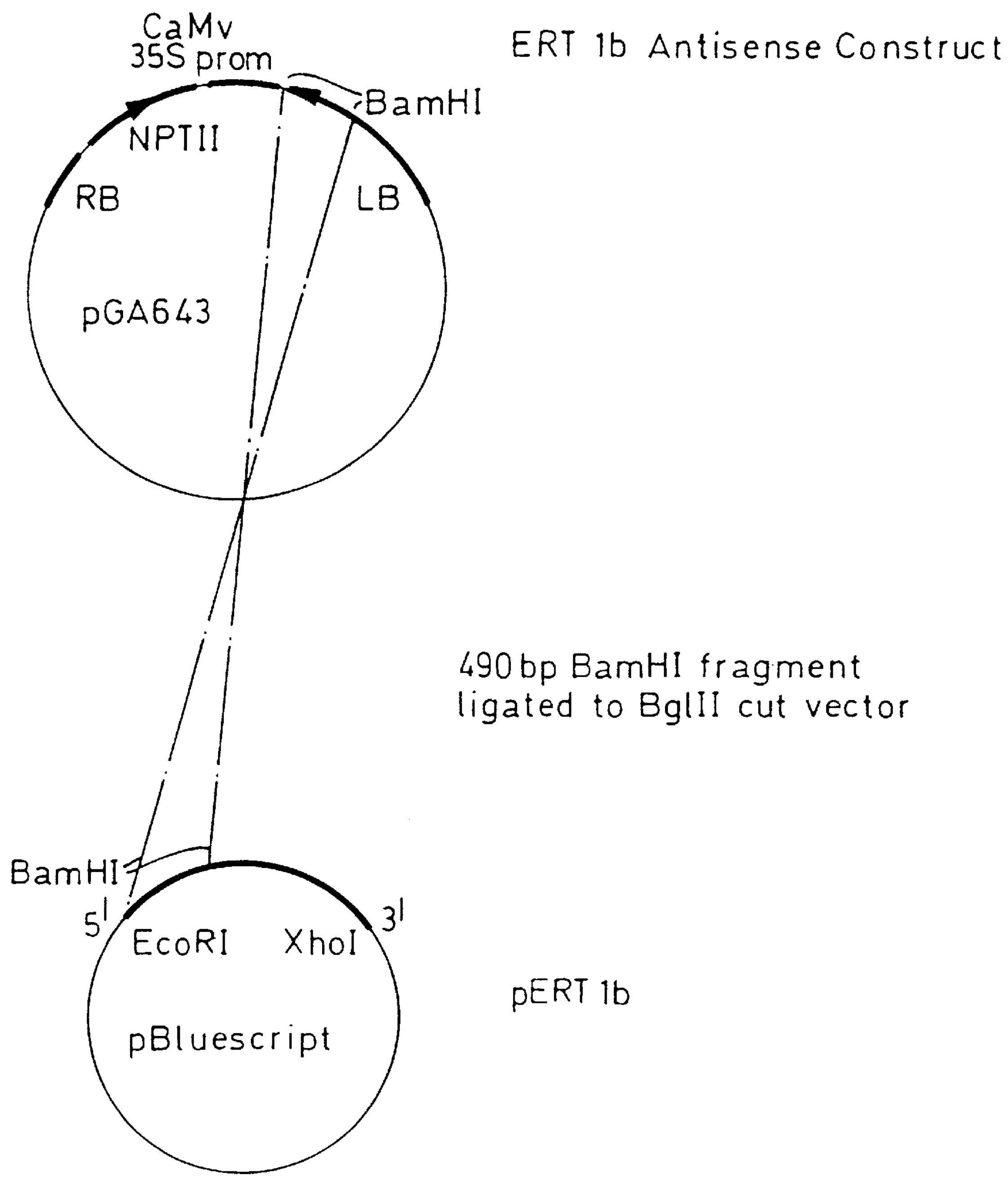
FIG. 3 is a diagram showing the construction of an ERT1b antisense construct.

FIG. 3 is a diagram showing the construction of an ERT1b antisense construct. pERT1b was digested with BamHI to release a 490 base pair fragment from the 5' end which was ligated into BglII-cut pGA643.

Figure 4:
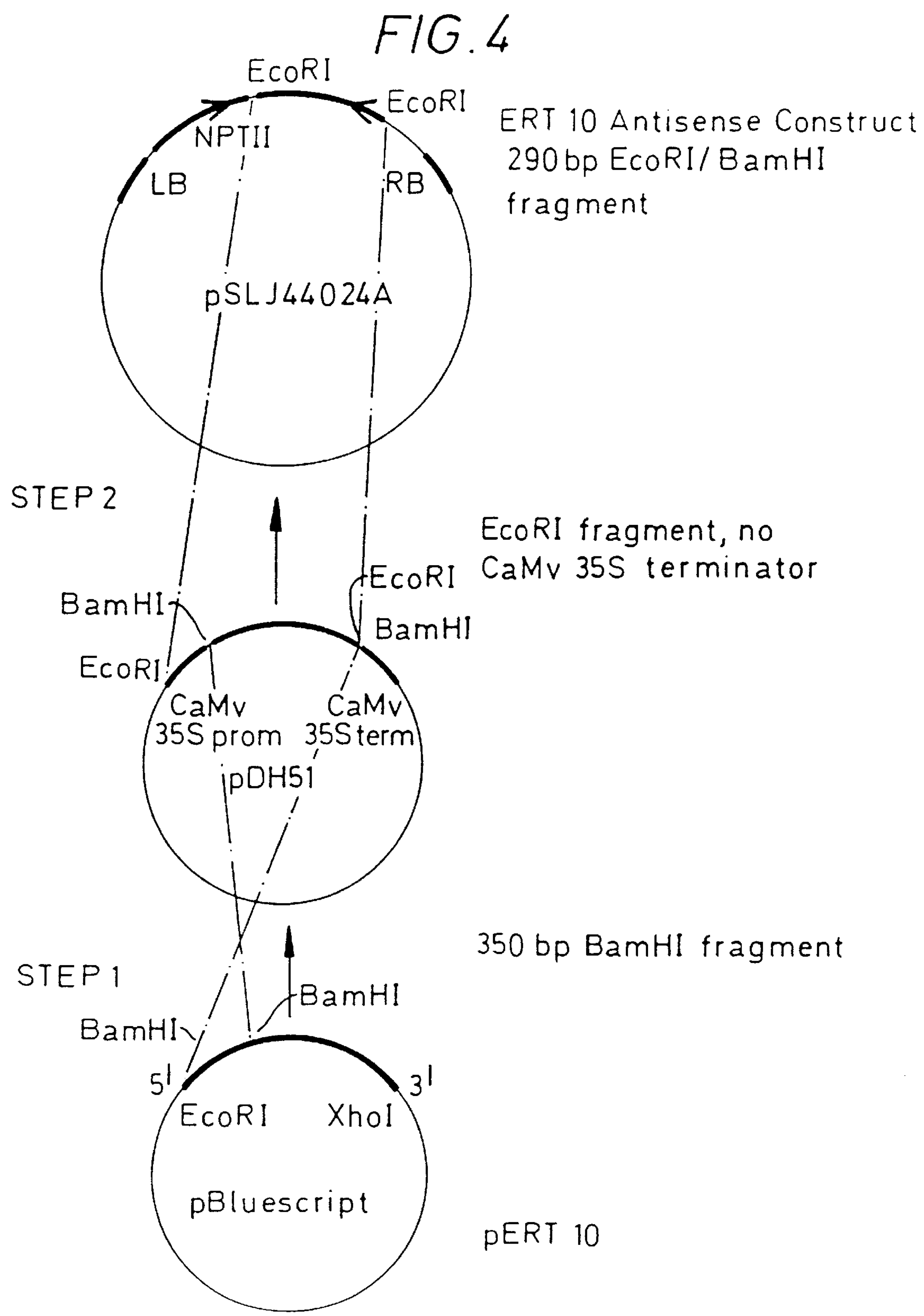
FIG. 4 is a diagram showing the construction of an ERT10 antisense construct without the CaMV 35S 3' end.

FIG. 4 is a diagram showing the construction of an ERT10 antisense construct without the CaMV 35S 3' end (terminator) pERT10 was digested with BamHI and the resulting 350 base pair fragment was cloned into BamHI-cut pDH51. The EcoRI fragment (missing 60 base pairs of ERT10 sequence) was removed from this vector and ligated into EcoRI-cut pSLJ44024A.

Figure 5:
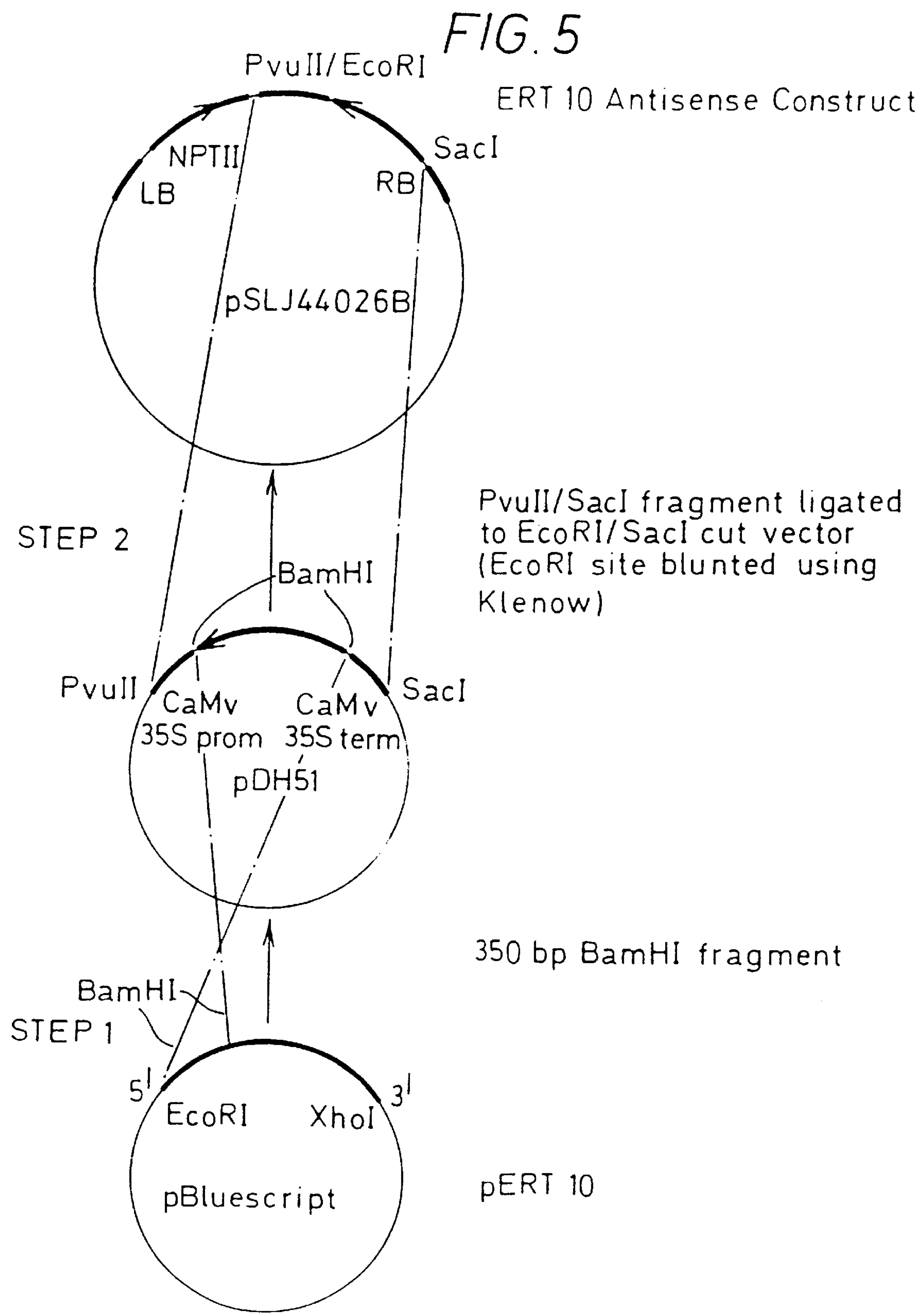
FIG. 5 is a diagram showing the construction of an ERT10 antisense construct with the CaMV 35S 3' end.

FIG. 5 is a diagram showing the construction of an ERT10 antisense construct with the CaMV 35S 3' end. pERT10 was digested with BamHI and the resulting 350 base pair fragment was cloned into BamHI-cut pDH51. Digestion of this vector with PvuII and SacI resulted in a fragment with the CaMV 35S 3' end intact. pSLJ44026B was digested initially with EcoRI and the resulting cohesive ends blunted using Klenow enzyme. The vector was then cut with SacI and the PvuII/SacI fragment ligated into it.

Figure 6:
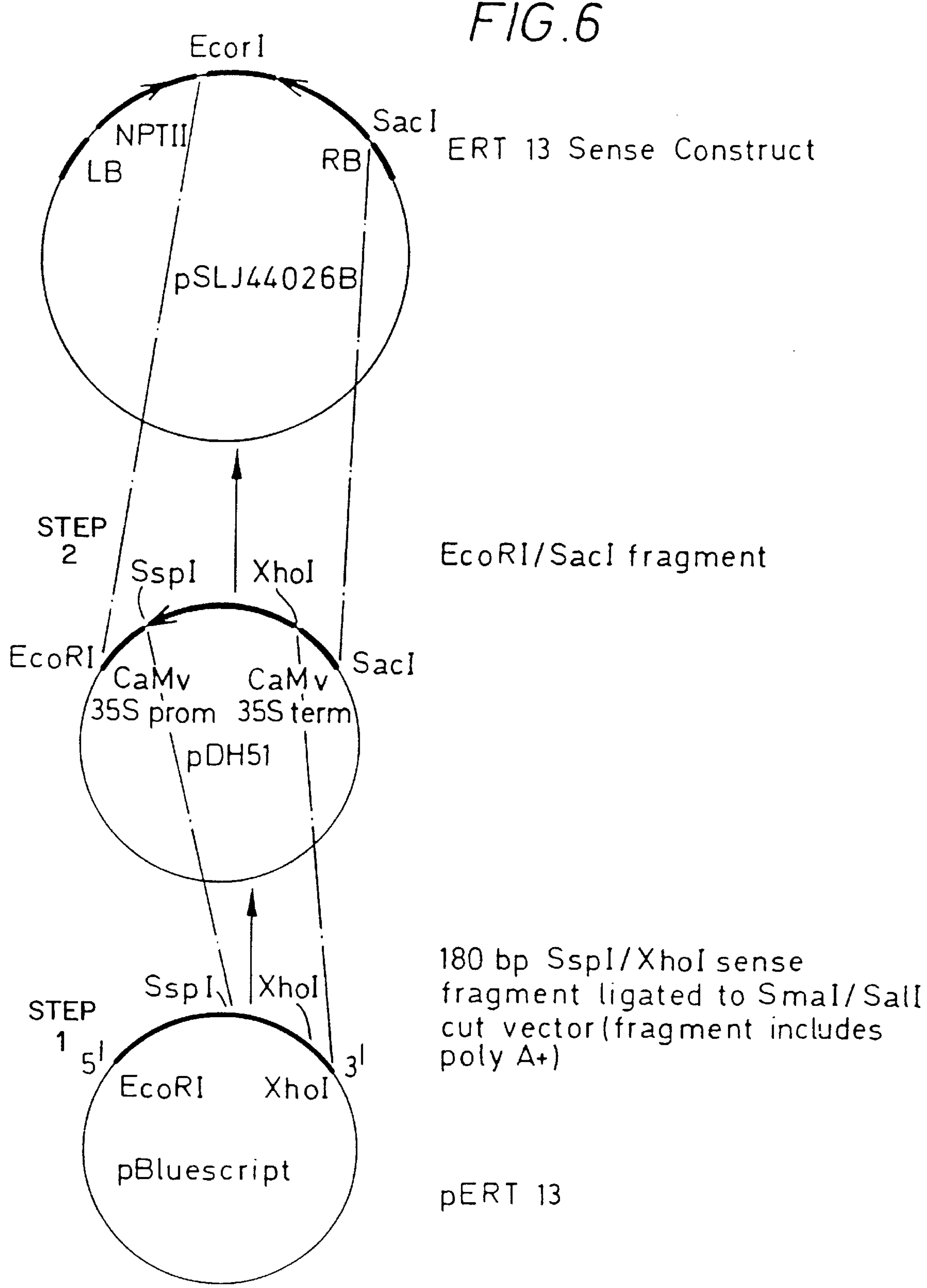
FIG. 6 is a diagram showing the construction of an ERT13 sense construct.

FIG. 6 is a diagram showing the construction of an ERT13 sense construct. pERT13 was digested with SspI and XhoI to release a 180 base pair fragment (including the PolyA+ tail). This was ligated into SmaI/SalI-cut pDH51 The EcoRI/SacI fragment was then cut from pDH51 and ligated into EcoRI/SacI pSLJ440426B.

Figure 7:
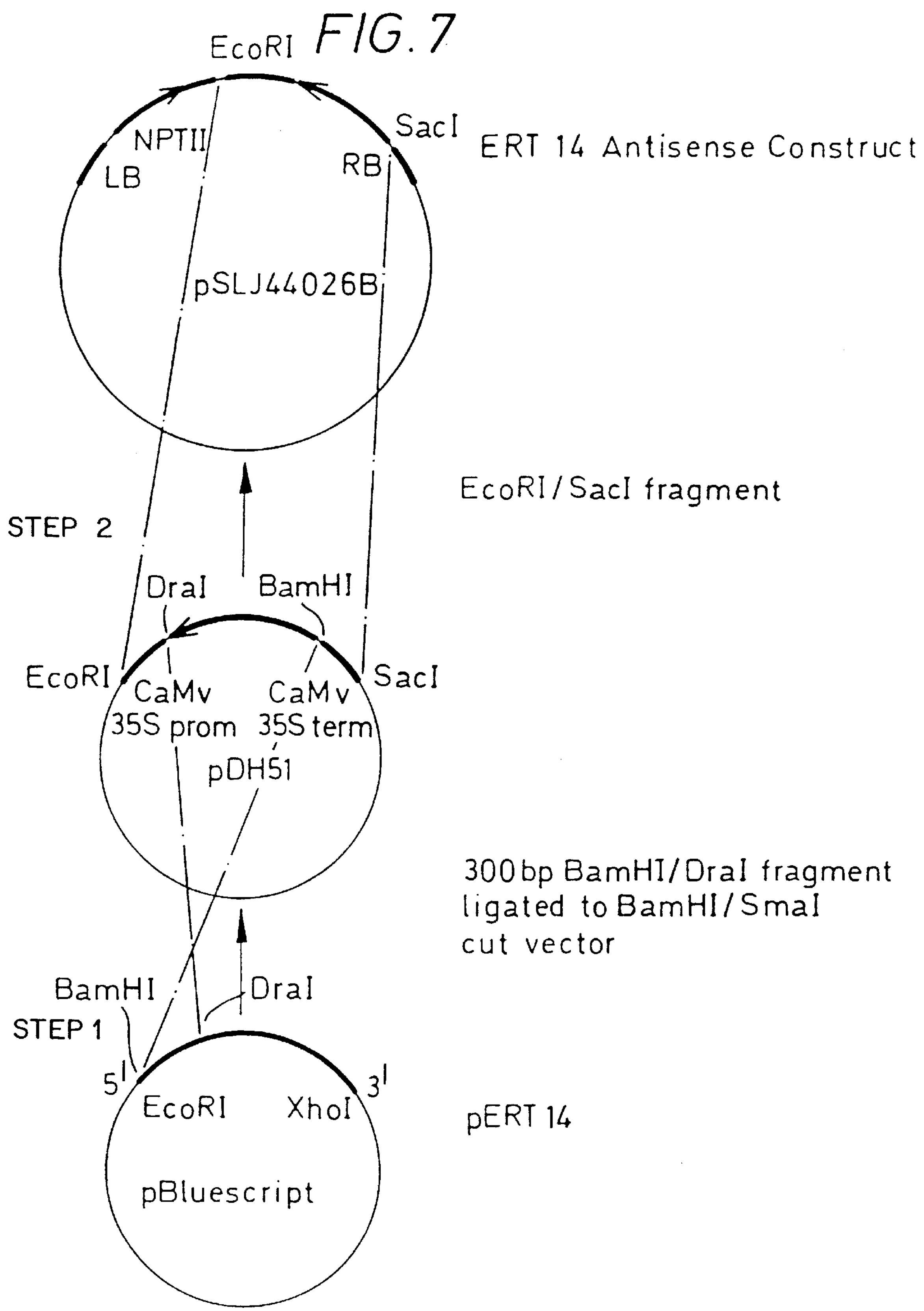
FIG. 7 is a diagram showing the construction of an ERT14 antisense construct.

FIG. 7 is a diagram showing the construction of an ERT14 antisense construct. pERT14 was digested with BamHI and DraI to release a 300 base pair fragment which was ligated into BamHX/SmaI-cut pDH51. The EcoRI/SacI fragment was removed from the vector and cloned into pSLJ44026B cut with EcoRI and SacI.

Figure 8:
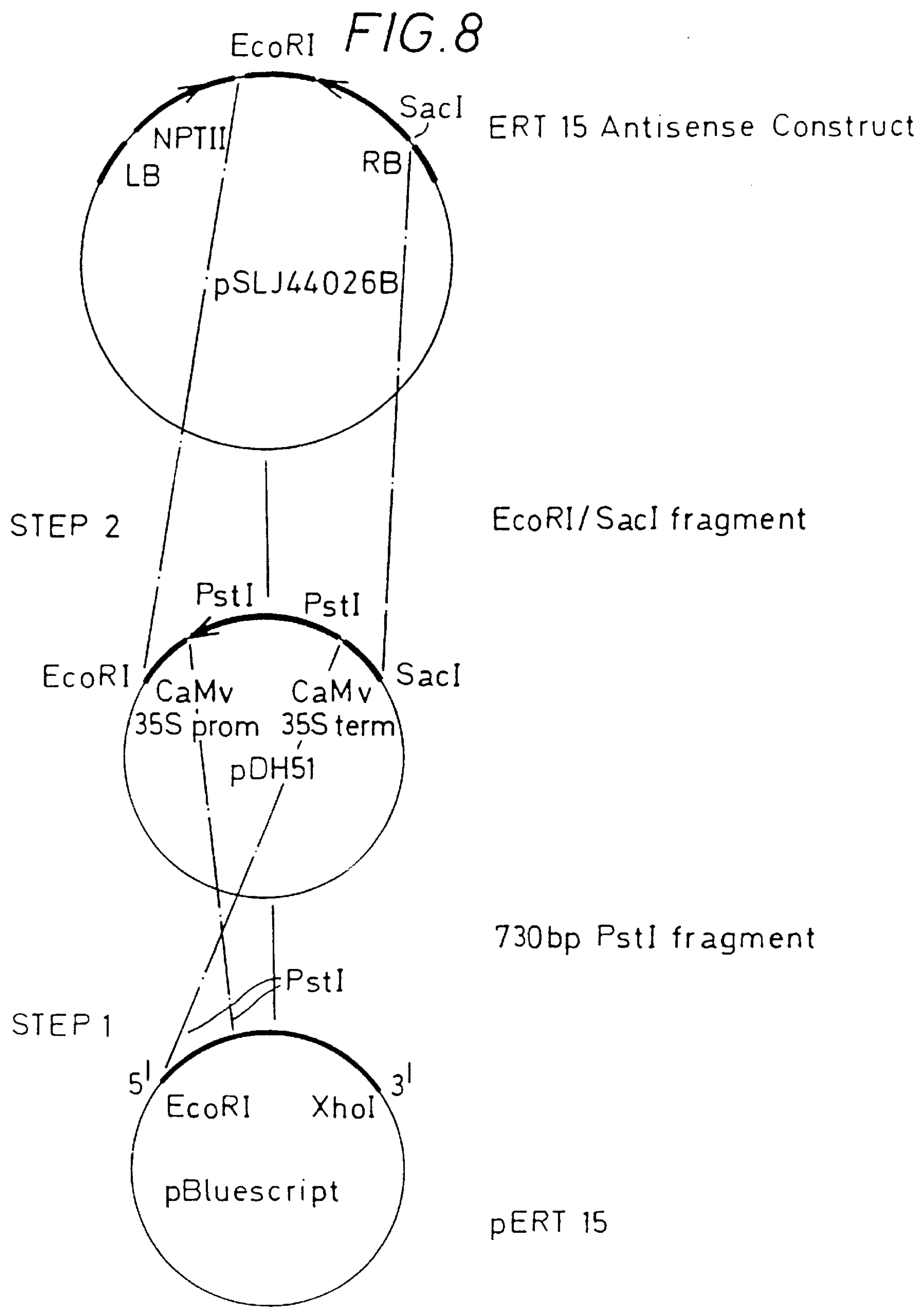
FIG. 8 is a diagram showing the construction of an ERT15 antisense construct.

FIG. 8 is a diagram showing the construction of an ERT15 antisense construct. pERT15 was digested with PstI to release a 730 base pair fragment which was cloned into PstI-cut pDH51. This vector was then cut with EcoRI and SacI and the fragment released was ligated into EcoRI/SacI-cut pSLJ44026B.

Figure 9:
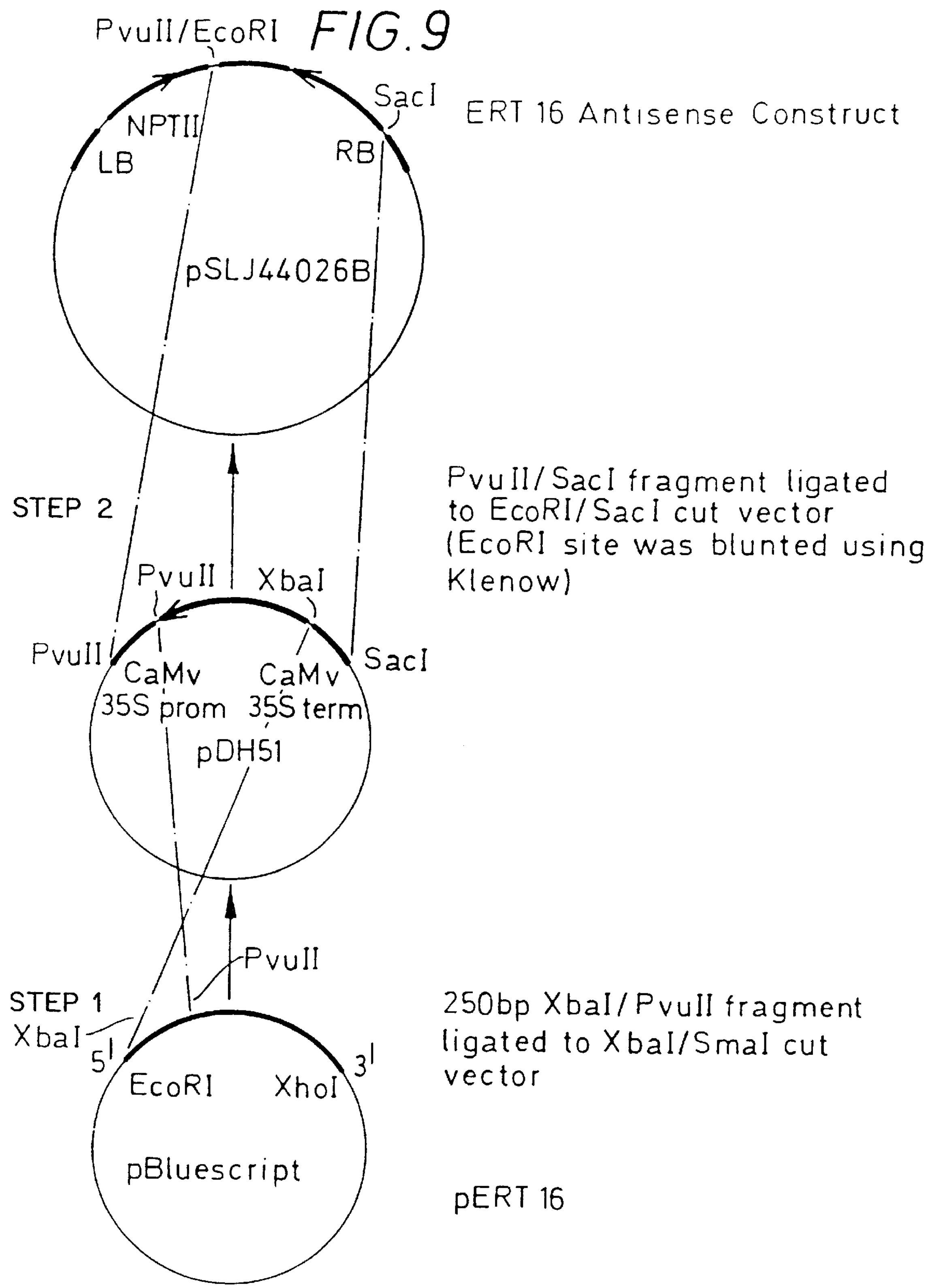
FIG. 9 is a diagram showing the construction of an ERT16 antisense construct.

FIG. 9 is a diagram showing the construction of an ERT16 antisense construct. pERT16 was digested with XbaI and PvuII to release a 250 base pair fragment which was cloned into XbaI/SmaI-cut pDH51. pSLJ44026B was initially digested with EcoRI and the resulting cohesive ends blunted using Klenow enzyme. This vector was then cut with SacI and the PvuII/SacI fragment cut from pDH51 ligated into it.

Figure 10:
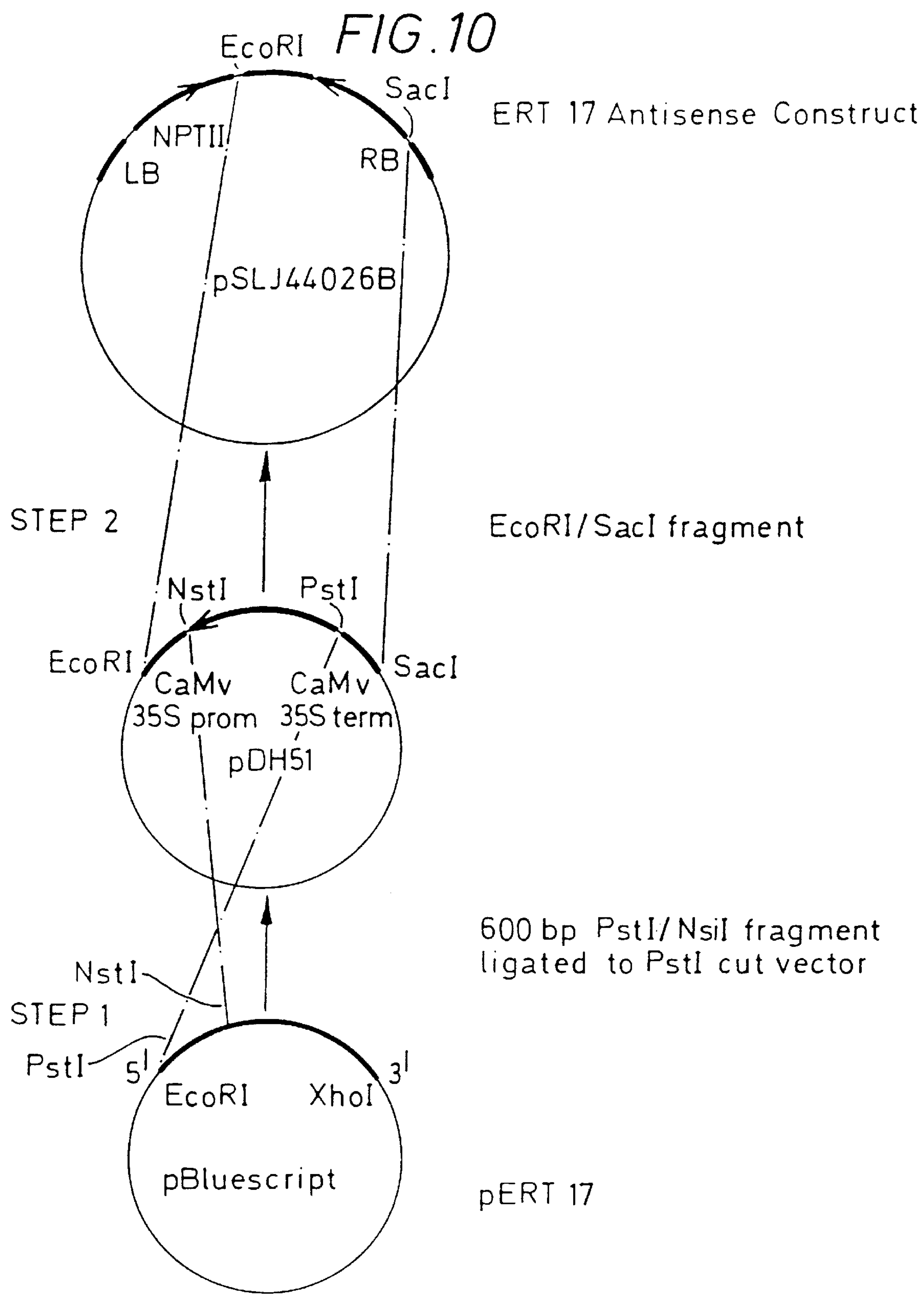
FIG. 10 is a diagram showing the construction of an ERT17 antisense construct.

FIG. 10 is a diagram showing the construction of an ERT17 antisense construct. pERT17 was digested with PstI and NsiI to release a 600 base pair fragment which was ligated into PstI-cut pDH51 EcoRI and SacI were used to digest pDH51 yielding a fragment which cloned into EcoRI/SacI-cut pSLJ44026B.

Figure 11:
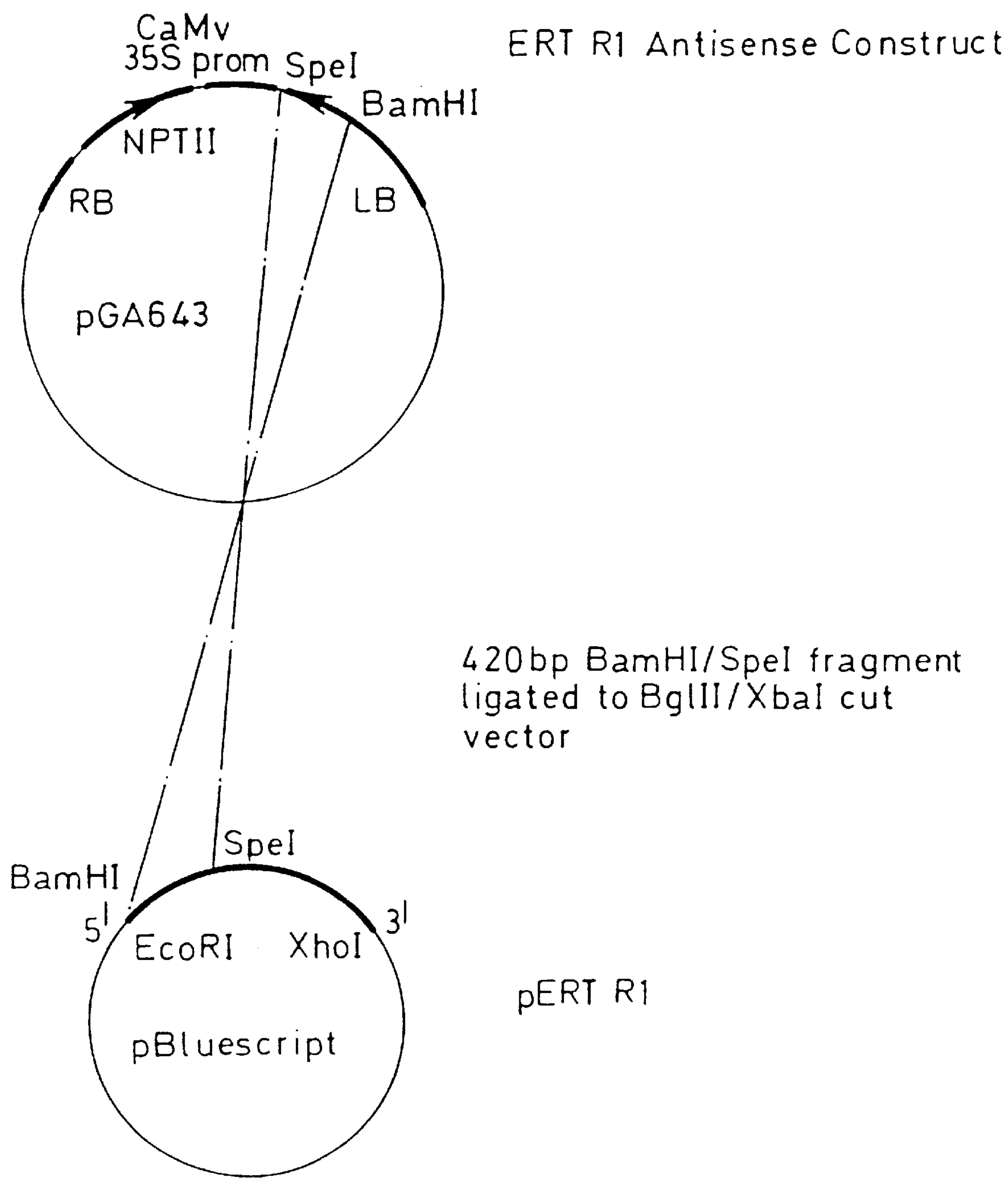
FIG. 11 is a diagram showing the construction of an ERT1 antisense construct.

FIG. 11 is a diagram showing the construction of an ERTR1 antisense construct. pERTR1 was digested with BamHI and SpeI to release a 420 base pair fragment which was ligated into BglII/XbaI-cut pGA643.

EXAMPLE 12

Generation of transformed plants

Vectors are transferred to *Agrobacterium tumefaciens* LBA4404 (a micro-organism widely available to plant biotechnologists) and are used to transform tomato plants.

Transformation of tomato cotyledons follows standard protocols (e g. Bird et al, 1988, Plant Molecular Biology, 11:651–662). Transformed plants are identified by their ability to grow on media containing the antibiotic kanamycin. Plants are regenerated and grown to maturity.

Ripening fruit are analysed for modifications to their ripening characteristics.

EXAMPLE 13

Transgenic plants

Table 1 summarises the numbers of plants which have been transformed using the various constructs described in Example 11. These plants and their fruit are currently being analysed. Progeny will also be developed and analysed. Further plants are being transformed.

TABLE 1

| CONSTRUCT | SIZE OF INSERT (bp) | NUMBER OF TRANSFORMED PLANTS |
|---|---|---|
| ERT1 no terminator (antisense) | 280 | 15 in compost (fruiting)<br>37 in tissue culture |
| ERT1 + terminator (antisense) | 340 | 14 in tissue culture |
| ERT1b (antisense) | 490 | 15 in compost (flowering)<br>15 in tissue culture |
| ERT10 no terminator | 290 | 15 in compost (fruiting)<br>47 in tissue culture |
| ERT13 (SENSE) | 180 | 11 in tissue culture |
| ERT14 (antisense) | 300 | 3 in tissue culture |
| ERT15 (antisense) | 730 | 15 in compost (flowering)<br>30 in tissue culture |
| ERT16 (antisense) | 250 | 5 in compost (flowering)<br>2 in tissue culture |
| ERT17 (antisense) | 600 | 9 in tissue culture |

We claim:

1. A DNA construct comprising the DNA sequence of an ERT clone selected from the group consisting of ERT1b, ERT10, ERT13, ERT14, ERT15, ERT17, ERTD1, ERTR1, and ERTS2.

2. A DNA construct as claimed in claim 1 in which the DNA sequence is under the control of a transcriptional initiation region operative in plants, so that the construct can generate RNA in plant cells.

3. A DNA construct as claimed in claim 1 which is a cDNA clone deposited at The National Collections of Industrial and Marine Bacteria (NCIMB) and selected from the group consisting of NCIMB 40544, NCIMB 40545, NCIMB 40546, NCIMB 40547, NCIMB 40548, NCIMB 40569, NCIMB 40588, NCIMB 40550, and NCIMB 40551.

4. A DNA construct as claimed in claim 1 which is a genomic DNA clone deposited at The National Collections of Industrial and Marine Bacteria (NCIMB) and selected from the group consisting of NCIMB 40606, NCIMB 40607, and NCIMB 40608.

5. A method of producing a plant cell expressing RNA from a DNA construct as claimed in claim 2 comprising transformation of a plant cell with a DNA construct as claimed in claim 2.

6. The method as claimed in claim 5 wherein said plant cell is from a fruit-bearing plant.

7. A method of producing an F1 hybrid plant comprising crossing two parent lines, at least one of which is a genetically modified plant homozygous for a DNA construct as claimed in claim 2.

8. A process of producing F1 hybrid seed comprising producing a genetically modified plant which is homozygous for a DNA construct as claimed in claim 2, crossing such a plant with a second homozygous variety, and recovering F1 hybrid seed.

9. A plant cell comprising a DNA construct as claimed in claim 2.

10. A plant derived from a plant cell as claimed in claim 9.

11. A fruit or seed comprising a DNA construct as claimed in claim 2.

12. A plant derived from a plant cell that is produced according to the method of claim 5.

* * * * *